(12) United States Patent
Robertson et al.

(10) Patent No.: US 7,923,207 B2
(45) Date of Patent: *Apr. 12, 2011

(54) APPARATUS AND SYSTEM HAVING DRY GENE SILENCING POOLS

(75) Inventors: Barbara Robertson, Boulder, CO (US); Devin Leake, Denver, CO (US); Kathryn Robinson, Golden, CO (US); William S. Marshall, Boulder, CO (US); Anastasia Khvorova, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 597 days.

This patent is subject to a terminal disclaimer.

(21) Appl. No.: 11/283,482

(22) Filed: Nov. 18, 2005

(65) Prior Publication Data

US 2006/0110829 A1 May 25, 2006

Related U.S. Application Data

(60) Provisional application No. 60/630,320, filed on Nov. 22, 2004, provisional application No. 60/678,165, filed on May 4, 2005.

(51) Int. Cl.
*C12Q 1/68* (2006.01)
*C07H 21/02* (2006.01)
*C07H 21/04* (2006.01)

(52) U.S. Cl. .......... 435/6; 536/23.1; 536/24.1; 536/24.5

(58) Field of Classification Search .................. None
See application file for complete search history.

(56) References Cited

U.S. PATENT DOCUMENTS

| | | | |
|---|---|---|---|
| 4,924,624 A | 5/1990 | Suhadolnik |
| 5,023,243 A | 6/1991 | Tullis |
| 5,138,045 A | 8/1992 | Cook |
| 5,151,510 A | 9/1992 | Stec |
| 5,166,320 A | 11/1992 | Wu et al. |
| 5,214,136 A | 5/1993 | Lin |
| 5,264,562 A | 11/1993 | Matteucci |
| 5,264,564 A | 11/1993 | Matteucci |
| 5,286,717 A | 2/1994 | Cohen |
| 5,399,676 A | 3/1995 | Froehler |
| 5,414,077 A | 5/1995 | Lin |
| 5,434,257 A | 7/1995 | Matteucci |
| 5,457,191 A | 10/1995 | Cook |
| 5,457,527 A | 10/1995 | Manns et al. |
| 5,459,255 A | 10/1995 | Cook |
| 5,484,908 A | 1/1996 | Froehler et al. |
| 5,487,872 A | 1/1996 | Hafeman et al. |
| 5,489,677 A | 2/1996 | Sangvhi |
| 5,502,177 A | 3/1996 | Matteucci |
| 5,514,786 A | 5/1996 | Cook |
| 5,532,130 A | 7/1996 | Alul |
| 5,578,718 A | 11/1996 | Cook |
| 5,580,767 A | 12/1996 | Cowsert |
| 5,587,361 A | 12/1996 | Cook |
| 5,587,469 A | 12/1996 | Cook |
| 5,587,470 A | 12/1996 | Cook |
| 5,591,721 A | 1/1997 | Agrawal |
| 5,594,121 A | 1/1997 | Froehler |
| 5,596,086 A | 1/1997 | Matteucci |
| 5,608,046 A | 3/1997 | Cook |
| 5,610,289 A | 3/1997 | Cook |
| 5,614,617 A | 3/1997 | Cook |
| 5,635,488 A | 6/1997 | Cook |
| 5,637,573 A | 6/1997 | Agrawal |
| 5,644,048 A | 7/1997 | Yau |
| 5,645,985 A | 7/1997 | Froehler |
| 5,652,355 A | 7/1997 | Metelev et al. |
| 5,652,356 A | 7/1997 | Agrawal |
| 5,658,731 A | 8/1997 | Sproat |
| 5,670,633 A | 9/1997 | Cook |
| 5,674,108 A | 10/1997 | Rolle |
| 5,674,908 A | 10/1997 | Haces et al. |
| 5,677,437 A | 10/1997 | Teng |
| 5,681,941 A | 10/1997 | Cook |
| 5,708,161 A | 1/1998 | Reese |
| 5,734,041 A | 3/1998 | Just |
| 5,750,666 A | 5/1998 | Caruthers |
| 5,756,710 A | 5/1998 | Stein |
| 5,757,710 A | 5/1998 | Li-Chun |

(Continued)

FOREIGN PATENT DOCUMENTS

EP 1114623 10/2001

(Continued)

OTHER PUBLICATIONS

U.S. Appl. No. 11/283,484, filed Nov. 18, 2005, Robertson et al.

(Continued)

*Primary Examiner* — Sean R McGarry
(74) *Attorney, Agent, or Firm* — Workman Nydegger

(57) ABSTRACT

A reverse transfection apparatus can be used for introducing siRNA into a cell to effect gene silencing. Such an apparatus can include a well plate having a well configured for transfecting cells. The well can include a substantially dry gene silencing composition that has at least two siRNAs which silences at least a first target gene. The gene silencing composition can be configured such that the at least two siRNAs are each capable of being solubilized or suspended in an aqueous medium in an amount sufficient for transfecting cells in the well. Additionally, the siRNAs can include a hairpin structure, modification, or a conjugate. Also, the at least siRNAs can be rationally designed. The reverse transfection apparatus can be provided as a kit or system that additionally includes cells, polynucleotide carriers, reverse transfection reagents, and the like.

19 Claims, 15 Drawing Sheets

U.S. PATENT DOCUMENTS

| | | |
|---|---|---|
| 5,763,588 A | 6/1998 | Metteucci |
| 5,767,264 A | 6/1998 | Otlvos |
| 5,770,713 A | 6/1998 | Imbach |
| 5,773,601 A | 6/1998 | Agrawal |
| 5,777,092 A | 7/1998 | Cook |
| 5,792,844 A | 8/1998 | Sangvhi |
| 5,792,847 A | 8/1998 | Bhur |
| 5,811,274 A | 9/1998 | Palsson |
| 5,811,534 A | 9/1998 | Cook |
| 5,817,781 A | 10/1998 | Swaminathan |
| 5,830,653 A | 11/1998 | Froehler |
| 5,834,439 A | 11/1998 | Haces et al. |
| 5,834,607 A | 11/1998 | Manoharan |
| 5,849,902 A | 12/1998 | Arrow |
| 5,852,182 A | 12/1998 | Cook |
| 5,852,188 A | 12/1998 | Cook |
| 5,856,455 A | 1/1999 | Cook |
| 5,859,221 A | 1/1999 | Cook |
| 5,872,232 A | 2/1999 | Cook |
| 5,883,237 A | 3/1999 | Stec |
| 5,889,136 A | 3/1999 | Scaringe et al. |
| 5,898,031 A | 4/1999 | Crooke |
| 5,912,339 A | 6/1999 | Miller |
| 5,914,396 A | 6/1999 | Cook |
| 5,919,619 A | 7/1999 | Tullis |
| 5,948,903 A | 9/1999 | Cook |
| 5,965,722 A | 10/1999 | Ecker |
| 5,973,136 A | 10/1999 | Agrawal |
| 5,989,835 A | 11/1999 | Dunlay et al. |
| 5,989,912 A | 11/1999 | Arrow |
| 5,998,203 A | 12/1999 | Matulic-adamic |
| 5,998,206 A | 12/1999 | Cowsert |
| 6,005,087 A | 12/1999 | Cook |
| 6,005,094 A | 12/1999 | Simon |
| 6,005,096 A | 12/1999 | Matteucci |
| 6,007,992 A | 12/1999 | Lin |
| 6,008,400 A | 12/1999 | Scaringe et al. |
| 6,028,183 A | 2/2000 | Lin |
| 6,043,352 A | 3/2000 | Manoharan |
| 6,060,592 A | 5/2000 | Acevedo |
| 6,110,916 A | 8/2000 | Haces et al. |
| 6,111,085 A | 8/2000 | Cook |
| 6,111,086 A | 8/2000 | Scaringe |
| 6,114,513 A | 9/2000 | Cook |
| 6,127,533 A | 10/2000 | Cook |
| 6,140,482 A | 10/2000 | Lyer |
| 6,143,881 A | 11/2000 | Metelev |
| 6,147,200 A | 11/2000 | Manoharan |
| 6,153,737 A | 11/2000 | Manoharan |
| 6,166,188 A | 12/2000 | Cook |
| 6,166,197 A | 12/2000 | Cook |
| 6,172,209 B1 | 1/2001 | Manoharan |
| 6,197,944 B1 | 3/2001 | Walder |
| 6,204,027 B1 | 3/2001 | Goodchild |
| 6,222,025 B1 | 4/2001 | Cook |
| 6,235,886 B1 | 5/2001 | Manoharan |
| 6,239,265 B1 | 5/2001 | Cook |
| 6,242,589 B1 | 6/2001 | Cook |
| 6,242,591 B1 | 6/2001 | Cole |
| 6,265,558 B1 | 7/2001 | Cook |
| 6,271,358 B1 | 8/2001 | Manoharan |
| 6,277,967 B1 | 8/2001 | Manoharan |
| 6,277,982 B1 | 8/2001 | Fraser |
| 6,300,319 B1 | 10/2001 | Manoharan |
| 6,307,040 B1 | 10/2001 | Cook |
| 6,322,987 B1 | 11/2001 | Cook |
| 6,326,358 B1 | 12/2001 | Manoharan |
| 6,331,441 B1 | 12/2001 | Balch et al. |
| 6,335,437 B1 | 1/2002 | Manoharan |
| 6,346,614 B1 | 2/2002 | Metelev |
| 6,348,312 B1 | 2/2002 | Peyman |
| 6,358,931 B1 | 3/2002 | Cook |
| 6,359,124 B1 | 3/2002 | Ecker |
| 6,369,040 B1 | 4/2002 | Acevedo |
| 6,369,209 B1 | 4/2002 | Manoharan |
| 6,380,368 B1 | 4/2002 | Froehler |
| 6,391,636 B1 | 5/2002 | Monia |
| 6,395,492 B1 | 5/2002 | Manoharan |
| 6,399,297 B1 | 6/2002 | Baker |
| 6,399,663 B1 | 6/2002 | Haces et al. |
| 6,403,781 B2 | 6/2002 | Cole |
| 6,410,702 B1 | 6/2002 | Swaminathan |
| 6,414,127 B1 | 7/2002 | Lin |
| 6,416,959 B1 | 7/2002 | Giuliano et al. |
| 6,420,546 B1 | 7/2002 | Seliger |
| 6,440,943 B1 | 8/2002 | Cook |
| 6,447,998 B1 | 9/2002 | Froehler |
| 6,451,991 B1 | 9/2002 | Martin |
| 6,458,940 B2 | 10/2002 | Roberts |
| 6,476,205 B1 | 11/2002 | Bhur |
| 6,485,974 B1 | 11/2002 | Papoff |
| 6,495,672 B1 | 12/2002 | Froehler |
| 6,506,559 B1 | 1/2003 | Fire |
| 6,514,464 B1 | 2/2003 | Knebel |
| 6,525,031 B2 | 2/2003 | Manoharan |
| 6,531,584 B1 | 3/2003 | Cook |
| 6,534,639 B1 | 3/2003 | Manoharan |
| 6,544,790 B1 | 4/2003 | Sabatini |
| 6,573,039 B1 | 6/2003 | Dunlay et al. |
| 6,576,752 B1 | 6/2003 | Manoharan |
| 6,590,093 B1 | 7/2003 | Scaringe |
| 6,600,032 B1 | 7/2003 | Manoharan |
| 6,608,035 B1 | 8/2003 | Agrawal |
| 6,620,591 B1 | 9/2003 | Dunlay et al. |
| 6,624,293 B1 | 9/2003 | Agrawal |
| 6,645,943 B1 | 11/2003 | Agrawal |
| 6,653,458 B1 | 11/2003 | Manoharan |
| 6,671,624 B1 | 12/2003 | Dunlay et al. |
| 6,673,611 B2 | 1/2004 | Thompson |
| 6,677,445 B1 | 1/2004 | Innis |
| 6,683,167 B2 | 1/2004 | Metelev |
| 6,716,582 B2 | 4/2004 | Gonye et al. |
| 6,716,588 B2 | 4/2004 | Sammak et al. |
| 6,716,882 B2 | 4/2004 | Haces et al. |
| 6,759,206 B1 | 7/2004 | Rubin et al. |
| 6,809,193 B2 | 10/2004 | McKay |
| 6,811,975 B2 | 11/2004 | Cook |
| 6,841,542 B2 | 1/2005 | Bartelmez |
| 6,846,921 B2 | 1/2005 | Innis |
| 6,875,578 B2 | 4/2005 | Giuliano et al. |
| 6,881,831 B2 | 4/2005 | Lyer |
| 6,902,883 B2 | 6/2005 | Dunlay et al. |
| 6,924,109 B2 | 8/2005 | Melcher et al. |
| 6,936,467 B2 | 8/2005 | Kmiec |
| 6,951,757 B2 | 10/2005 | Sabatini |
| 6,958,239 B2 | 10/2005 | Arrow |
| 6,977,245 B2 | 12/2005 | Klinman |
| 7,045,609 B2 | 5/2006 | Metelev |
| 7,067,497 B2 | 6/2006 | Hanecak |
| 7,078,196 B2 | 7/2006 | Tuschl |
| 7,173,014 B2 | 2/2007 | Agrawal |
| 7,595,387 B2 | 9/2009 | Leake et al. |
| 2002/0006664 A1 | 1/2002 | Sabatini |
| 2002/0128466 A1 | 9/2002 | Cole |
| 2002/0160379 A1 | 10/2002 | Cook |
| 2003/0036516 A1 | 2/2003 | Agrawal |
| 2003/0045698 A1 | 3/2003 | Manoharan |
| 2003/0096770 A1 | 5/2003 | Krotz |
| 2003/0135033 A1 | 7/2003 | Klippel-Giese |
| 2003/0170642 A1 | 9/2003 | Caldwell et al. |
| 2003/0170891 A1 | 9/2003 | McSwiggen |
| 2003/0190626 A1 | 10/2003 | Ravikumar |
| 2003/0203486 A1 | 10/2003 | Sabatini |
| 2003/0206887 A1* | 11/2003 | Morrissey et al. ............ 424/93.2 |
| 2003/0228601 A1 | 12/2003 | Sabatini |
| 2003/0228694 A1 | 12/2003 | Sabatini |
| 2004/0009938 A1 | 1/2004 | Manoharan |
| 2004/0014108 A1 | 1/2004 | Eldrup |
| 2004/0014956 A1 | 1/2004 | Woolf |
| 2004/0014957 A1 | 1/2004 | Eldrup |
| 2004/0019008 A1 | 1/2004 | Lewis et al. |
| 2004/0043948 A1 | 3/2004 | Baker |
| 2004/0053875 A1 | 3/2004 | Kruetzer |
| 2004/0054155 A1 | 3/2004 | Woolf |
| 2004/0058886 A1 | 3/2004 | Scaringe |
| 2004/0072779 A1 | 4/2004 | Kruetzer |
| 2004/0096880 A1 | 5/2004 | Kmiec |

| | | | |
|---|---|---|---|
| 2004/0102408 | A1 | 5/2004 | Kruetzer |
| 2004/0110296 | A1 | 6/2004 | Vargeese |
| 2004/0137064 | A1 | 7/2004 | Lewis et al. |
| 2004/0147022 | A1 | 7/2004 | Baker |
| 2004/0147023 | A1 | 7/2004 | Baker |
| 2004/0167090 | A1 | 8/2004 | Monaharan |
| 2004/0180351 | A1 | 9/2004 | Giese |
| 2004/0198640 | A1 | 10/2004 | Leake |
| 2004/0204420 | A1 | 10/2004 | Rana |
| 2004/0248299 | A1 | 12/2004 | Jayasena |
| 2004/0266707 | A1 | 12/2004 | Leake et al. |
| 2004/1259247 | | 12/2004 | Tuschl et al. |
| 2005/0020521 | A1 | 1/2005 | Rana |
| 2005/0020525 | A1 | 1/2005 | McSwiggen |
| 2005/0026160 | A1 | 2/2005 | Allerson |
| 2005/0059044 | A1 | 3/2005 | Graham |
| 2005/0130181 | A1 | 6/2005 | McSwiggen |
| 2005/0181385 | A1 | 8/2005 | Linsley |
| 2005/0223427 | A1 | 10/2005 | Leake |
| 2005/0239728 | A1 | 10/2005 | Pachuk et al. |
| 2005/0255487 | A1 | 11/2005 | Khorova |
| 2006/0110766 | A1 | 5/2006 | Robertson et al. |
| 2006/0115461 | A1 | 6/2006 | Robertson et al. |
| 2006/0127891 | A1 | 6/2006 | McSwiggen |
| 2006/0166234 | A1 | 7/2006 | Robertson et al. |
| 2006/0178324 | A1 | 8/2006 | Hadwiger |
| 2006/0223777 | A1 | 10/2006 | Vermeulen |
| 2007/0141134 | A1 | 6/2007 | Kosak |
| 2007/0167384 | A1 | 7/2007 | Leake |
| 2007/0173476 | A1 | 7/2007 | Leake |
| 2007/0269889 | A1 | 11/2007 | Leake |

FOREIGN PATENT DOCUMENTS

| | | |
|---|---|---|
| EP | 1389637 | 2/2004 |
| EP | 1559785 | 8/2005 |
| EP | 1814895 | 8/2007 |
| WO | 93-04204 | 3/1993 |
| WO | 94-01550 | 1/1994 |
| WO | 94-21825 | 9/1994 |
| WO | 94-26887 | 11/1994 |
| WO | WO 97/30731 | 8/1997 |
| WO | WO9742819 | 11/1997 |
| WO | 99-32619 | 7/1999 |
| WO | WO0012454 | 3/2000 |
| WO | WO0120015 | 3/2001 |
| WO | 01-75164 | 10/2001 |
| WO | 02-44321 | 6/2002 |
| WO | 02-094185 | 11/2002 |
| WO | 03-064625 | 8/2003 |
| WO | 03-064626 | 8/2003 |
| WO | 03-070193 | 8/2003 |
| WO | 03-070918 | 8/2003 |
| WO | 03-072705 A2 | 9/2003 |
| WO | 03-072705 A3 | 9/2003 |
| WO | 03-074654 | 9/2003 |
| WO | WO 2004/009847 | 1/2004 |
| WO | 2004-015107 A2 | 2/2004 |
| WO | 2004-015107 A3 | 2/2004 |
| WO | WO2004011624 | 2/2004 |
| WO | WO2004045543 | 6/2004 |
| WO | 2004-080406 | 9/2004 |
| WO | WO2004078946 | 9/2004 |
| WO | 2004-091515 | 10/2004 |
| WO | WO2004090105 | 10/2004 |
| WO | 2004-109290 | 12/2004 |
| WO | 2005-019453 | 3/2005 |
| WO | WO 2005/039645 | 5/2005 |
| WO | WO2005078094 | 8/2005 |
| WO | WO2005097992 | 10/2005 |
| WO | WO 2006/058046 | 6/2006 |
| WO | WO 2006/058048 | 6/2006 |
| WO | WO 2006/060246 | 6/2006 |
| WO | WO 2006/071410 | 7/2006 |

OTHER PUBLICATIONS

U.S. Appl. No. 11/283,481, filed Nov. 18, 2005, Robertson et al.
U.S. Appl. No. 11/283,483, filed Nov. 18, 2005, Robertson et al.
Silva et al., RNA Interference Microarrays, High-Throughput Loss-of-Function Genetics in Mammalian Cells. PNAS. Apr. 27, 2004, vol. 101, No. 17, pp. 6548-6552.
VanHecke et al., High-Throughput Gene Silencing Using Cell Arrays, Oncogene, 2004, vol. 23, pp. 8353-8358.
Mousses et al., PNAi Microarry Analysis in Cultured Mammalian Cells, Genome Research, 2003, vol. 13, pp. 2341-2347.
Kumar et al., High-throughput selection of effective RNAi probes for gene silencing, Genome Research, 2003, vol. 13, pp. 2333-2340.
Mousses et al., RNAi microarray analysis in cultured mammalian cells, Genome Research, 2003, vol. 13, pp. 2341-2347.
Bailey et al, Applications of transfected cell microarrays in high-throughput drug discovery, Drug Discovery Today, 2002, vol. 7, pp. S113-S118.
Homna et al., The role of atelococollagen-based cell transfection arry in high-throughput screening of gene functions and in drug discover, Curreng Drug Discovery Technologies, Dec. 2004, vol. 1, pp. 287-294.
Office Action dated Mar. 21, 2007 from U.S. Appl. No. 11/283,484 (Robertson et al.), 15 pages.
International Search Report from PCT/US2005/042404, Mar. 7, 2007, 2 pages.
International Preliminary Report on Patentability from PCT/US2006/042404, May 22, 2007, 5 pages.
Written Opinion from PCT/US2006/042404, Mar. 7, 2007, 4 pages.
International Search Report from PCT/US2005/042407, Sep. 8, 2006, 2 pages.
International Preliminary Report on Patentability from PCT/US2005/042407, May 22, 2007, 4 pages.
Written Opinion from PCT/US2005/042407, Jun. 20, 2006, 3 pages.
International Search Report from PCT/US2005/042385, Apr. 5, 2007, 3 pages.
International Preliminary Report on Patentability from PCT/US2005/042385, May 22, 2007, 4 pages.
Written Opinion from PCT/US2005/042385 Jan. 29, 2007, 3 pages.
International Search Report from PCT/US2005/042403, Sep. 28, 2006, 4 pages.
International Preliminary Report on Patentability from PCT/US2005/042403, May 22, 2007, 4 pages.
Written Opinion from PCT/US2005/042403, Jun. 8, 2006, 3 pages.
Vermeulen, A. et al., "The contributions of dsRNA structure to Dicer specificity and efficiency", RNA,11:674-682 (2005).
*Atlas Venture*, Dharmacon and Akceli Announce Research Collaboration to Combine Reverse Transfection and siRNA for High Throughput Gene Silencing, www.atlasventure.com/home/news_content.asp?ne_id=1741 (Aug. 24, 2004).
Ambion, High Throughput siRNA Deliery In Vitro: From Cell Lines to Pimrary Cells, TechNotes 12(2); ww.ambion.com/techlib/tn/122/3.html downloaded Jul. 18, 2005).
*Boston Business Journal*, "Biotech firm Akceli wins first patent," www.bizhournals.com/boston/stories/2003/04/07/daily13.html.
Dhellin, Olivier et al., "Functional differences between the human LINE retrotransposon and retroviral revsere transcriptases for in vivo mRNA reverse transcription," The EMBO Journal, vol. 16, pp. 6590-6602; 1997.
Press Release, Dharmacon Launches siArray RTF™ siRNA Librar-ies—First-Ever Using Reverse Transfection Technology, qb Perbio Solutions for Life Science; Layfayette, Colo; Apr. 22, 2005.
Hannon, Gregory J., "RNA Interference," Nature, vol. 418; Jul. 11, 2002. (www.nature.com/nature).
Ketting, R.F. et al. (2001) Dicer Functions in RNA Interference and in Synthesis of Small RNA Involved in Developmental Timing in *C. elegans* Genes Dev., Oct. 15, 2001, 15(20):2654-9.
Paddison, P. J., et al., "A resource for large-scale RNA-interference-based screens in mammals," Nature, vol. 428; Mar. 25, 2004 (www.nature.com/nature).
He, L. et al., "MicroRNAs: Small RNAs with a Big Role in Gene Regulation," Nature, vol. 5, pp. 522-532; Jul. 2004 (www.nature.com/reviews/genetics).
Hannon, G.J., et al., "Unlocking the Potential of the Human Genome with RNA Interference," Nature, vol. 431; Sep. 16, 2004 (www.nature.com/nature).

Hammond, S.M., et al., "Post-Transcriptional Gene Silencing by Double-Stranded RNA," *Nature*, vol. 2; Feb. 2001 (www.nature.com/reviews/genetics).

Hannon, G., "Growth control in mammalian cells: post-transcriptional gene silencing," (www.cshl.org/public/SCIENCE/hannon.html) (2004).

Denli, A.M., et al., "RNAi: an ever-growing puzzle," *TRENDS in Biochemical Sciences*, vol. 28, No. 4, Apr. 2003.

Silva, J.M., et al., "RNA interference: a promising approach to antiviral therapy?" *Trends in Molecular Medicine*, vol. 8, No. 11, Nov. 2002.

Qiagen Website (www.qiagen.com), Transfection Cell Database, Using siRNA (dsRNA) as Nucleic Acid, Cell Records.

"The HiPerformance algorithm designs highly potent and specific siRNA", Technical Information, www1.qiagen.com/literature/resources/RNAi/1030174_TI_GS_siRNA_0105.pdf; downloaded Jul. 18, 2005.

Ziauddin, J. et al., "Microarrays of cells expressing defined cDNAs," Letters to Nature, *Nature*, 411, pp. 107-110 (May 3, 2001); doi:10.1038/35075114.

Reverse Transfection Homepage and Guide, Ziauddin, J. and Sabatini, D., http://staffa.wi.mit.edu/sabatini_public/reverse/transfection/content (downloaded Aug. 24, 2004).

Product Insert, siARRAY™ siRNA Libraries, Version 2.0; Dharmacon RNA Technologies.

SuperArray Bioscience Corporation, Introducing siRNA Array Plates, www.supperarray.com/RNAiArrayPlates.php (downloaded Jul. 18, 2005).

SuperArray Bioscience Corporation, siRNA Array Plates, www.supperarray.com/manuals/Present_ArrayPlates.pdf (downloaded Jul. 18, 2005).

SuperArray Bioscience Corporation, Newly Released SureSilencing™ Mouse siRNA Products, www.supperarray.com/siRNAnew.php?sp=Mouse (downloaded Jul. 18, 2005).

SuperArray Bioscience Corporation, Newly Released SureSilencing™ Human siRNA Products, www.supperarray.com/siRNAnew.php?sp=Human (downloaded Jul. 18, 2005).

QIAGEN, Transfection Reagent Selector Kit Handbook, Jan. 1999.

Bernstein, E., et al., "The rest is silence," *RNA* (2001), 7:1509-1521. Cambridge University Press.

U.S. Appl. No. 11/857,732, filed Sep. 19, 2007, Khvorova.

Amarzguioui et al., Tolerance for Mutations and Chemical Modifications in siRNA, 2003, Nucleic Acids Research, vol. 31, No. 2, pp. 589-595 Oxford University Press.

Parrish et al., Functional Anatomy of a dsRNA Trigger: Differential Requirement for the Two Trigger Strands in RNA Interference, Nov. 2000, Molecular Cell, vol. 6, pp. 1077-1087.

Elbashir et al., RNA Interference is Mediated by 21- and 22-Nucleotide RNAs, Jan. 2001, Genes & Development, vol. 15, pp. 188-200.

Letsinger et al., Cholesteryl-conjugated Oligonucleotides: Synthesis, properties, and activity as inhibitors of replication of human immunodeficiency virus in cell culture, Sep. 1989, Proc. Natl. Acad. Sci. vol. 86, pp. 6553-6556.

Boiziau et al. (1995) Antisense 2"-O-alkyl Oligoribinucleotides are efficient inhibitors of reverse transcription, Nucleic Acids Res. 23/1:64-71.

Chiu et al. (2003) siRNA function in RNAi: A Chemical Modification Analysis, RNA 9/9:1034-1048.

Conrad et al. (1995) Enzymatic synthesis of 2'-modified nucleic acids: identification of important phosphate and ribose moieties in Rnase P substrates, Nucleic Acids Res. 23/11:1845-1853.

Czauderna et al. (2003) Structural Variations and Stabilizing modifications of synthetic siRNAs in mammalian cells, Nucleic Acids Res. 31/11:2705-2716.

Grunweller et al. (2003) Comparison of different antisense strategies in mammalian cells using locked nucleic acid, 2'-O-methyl RNA, phosphorothioates and small interfering RNA, Nucleic Acids Res. 31/12:3185-3193.

Holen et al. (2003) Similar behavior of single-strand and double-strand siRNAs suggests they act through a common RNAi pathway, Nucleic Acids Res. 31/9:2401-2407.

Johansson et al. (1994) Target-specific arrest of mRNA translation by antisense 2'-O-Alkyloligoribonucleotides, Nucleic Acids Res. 22/22:4591-4598.

Larrouy et al. (1995) Rnase H is responsible for the non-specific inhibition of in vitro translation by 2'-O-alkyl chimeric oligonucleotides: high affinity or selectivity, a dilemma to design antisense oligomers, Nucleic Acids Res. 23/17:3434-3440.

Liang, L. et al (2002) Optimizing the delivery systems of chimeric RNA-DNA oligonucleotides: Beyond general oligonucleotide transfer, Eur J. Biochem 269:5953-5758.

Majlessi et al. (1998) Advantages of 2'-O-methyl oligoribonucleotide probes for detecting RNA targets, Nuclic Acids Res.26/9:2224-2229.

Monia et al. (1993) Evaluation of 2'-Modified Oligonucleotides Containing 2'-Deoxy gaps as Antisense Inhibitors of Gens Expression, J. Biol. Chem. 268/19:14514-14522.

Nykanen et al. (2001) ATP Requirements and Small Interfering RNA Structure in the RNA Interference Pathway, Cell 107:309-321.

Stump et al. (1999) The use of modified primers to eliminate cycle sequencing artifacts, Nucleic Acids Res. 27/23:4642-4648.

Uchiyama et al. (1994) Studies of the Interactions Between *Escherichia coli* Ribonuclease HI and Its Substrate, J Mol. Biol. 243:782-791.

Braasch, D. et al (2003) "RNA Interference in Mammalian Cells by Chemically-modified RNA" Biochemistry 42/26:7967-7995.

Harborth, J. et al. (Apr. 2003) "Sequence, Chemical, and Structural Cariation of Small Interfering RNAs and Short Harpin RNAs and the Effect on Mammalian Gene Silencing" Antisense & Nucleic Acid Drug Development 13/2:83-105.

Elbashir, S. M. et al (2001) Functional Anatomy of siRNAs for Mediating efficient RNAi in *Drosophila melanogaster* embyro lysate, The EMBO Journal 20/23:6877-6888.

Jackson, A. L. et al. (2003) Expression Profiling Reveals off-target Gene Regulation by RNAI, Nature Biotechnology 21/6:635-637.

Lubini et al. Stabilizing effects of the RNA 2'-sustitutent Crystal Structure of an Oligodeoxynucleotide duplex Containing 2'-O-methylated adenosines Chem. Biol. 1004 September 1(1): 39-45.

Dharmacon RNA Technologies, Dharmacon and Merck's Rosetta Collaborate to Assess Multiple Factors Affecting Efficacy and Specificity of siRNA for Gene Silencing, Oct. 8, 2003, Press Release, Layfette, CO.

Rosetta siRNA Experiments Performed in 2007, pp. 1-11.

Rossi, J., "A Cholesterol Connection in RNAi," Nature, Nov. 2004, vol. 432, pp. 155-156.

Soutscheck, J., et al., "Therapeutic Silencing of an Endogenous Gene by Systemic Administration of Modified siRNAs," Nature, Nov. 2004, vol. 432, pp. 173-178.

Kim, D. H. et al., Synthetic dsRNA Dicer Substrates Enhance RNAi Patency and efficacy, Nature Biotechnology, Advanced Online Publication, (2004), p. 1-5, Published Online Dec. 26, 2004.

Paddison, Patrick J. et al., "Short hairpin RNAs shRNAs) induce sequence-specific silencing in mammalian cells", Genes & Development 16, (2002), p. 946-958.

Zhang, Haidi et al., "Human Dicer Preferentially cleaves dsRNAs at their termini without a requirement for ATP", The EMBO Journal vol. 21, No. 21, (2002), p. 5875-5885.

Hohjoh, Hirohiko, "Enhancement of RNAi activity by improved siRNA duplexes", FEBS letters 557, (2004), p. 193-198.

Jin-Baio et al., "Structural basis for overhanging-specific small interfering RNA recognition by PAZ domain", Nature, vol. 429, May 20, 2004, p. 318-322.

Siolas, Despina, "Synthetic shRNAs as potent RNAi triggers", Nature Biotechnology, p. 1-5, published online Dec. 26, 2004.

Zeng, Yan et al., "Both Natural and Designed Micro RNAs Technique Can Inhibit the Expression of Cognate mRNAs When Expressed in Human Cells", Molecular Cell, vol. 9, Jun. 2002, p. 1327-1333.

Holen et al. (2002) Positional Effects of short interfering RNAs targeting the human coagulation trigger Tissue Factor, Nucleic Acid Research, 30/8:1757-1766.

International Search Report from PCT/US05/011008, Mar. 31, 2005, 5 Pages.

Written Opinion from PCT/US05/011008, Mar. 31, 2005, 6 Pages.

International Search Report from PCT/US05/003365, Apr. 2, 2005, 7 Pages.

Written Opinion from PCT/US05/003365, Apr. 2, 2005, 10 Pages.
Notification Regarding Review of Justification for Invitation to Pay Additional Fees from PCT/US05.003365, Apr. 2, 2005, 4 Pages.
SuperArray SureSilencing Array Plates User Manual (Version 1.0 Feb. 13, 2004)—SureSilencing Array Plates; Validated Gene-Specific siRNA for Pathway Profiling by Reverse Transfection; Frederick, MD, USA.
SuperArray SureSilencing Array Plates User Manual (Version 1.1 Mar. 5, 2004)—SureSilencing Array Plates; Validated Gene-Specific siRNA for Pathway Profiling by Reverse Transfection; Frederick, MD, USA.
Minakuchi, Yoshiko, et al., Atelocollagen-Mediated Synthetic Small Interfering RNA Delivery for Effective Gene Silencing In Vitro and In Vitro, Nucleic Acids Research, 2004, vol. 32, No. 13, Oxford University Press 2004, pp. 1-7, Published online Jul. 22, 2004.
Yoshikawa, Tomohiro, et al., Transfection Microarray of Human Mesenchymal Stem Cells and On-Chip siRNA Gene Knockdown, Journal of Controlled Release 96 (2004), pp. 227-232.
U.S. Appl. No. 11/283,484, Mail Date Sep. 17, 2009, Office Action.
U.S. Appl. No. 11/283,483, Mail Date Dec. 28, 2009, Office Action.
U.S. Appl. No. 11/283,481, Mail Date Oct. 15, 2009, Office Action
U.S. Appl. No. 11/283,481, Mail Date May 11, 2010, Office Action.
Office Action from U.S. Appl. No. 11/283,481, dated Oct. 15, 2009.
Office Action from U.S. Appl. No. 11/283,481, dated May 11, 2010.
Notice of Allowance from U.S. Appl. No. 11/283,481, dated Aug. 30, 2010.
Office Action from U.S. Appl. No. 11/283,483, dated Dec. 11, 2007.
Office Action from U.S. Appl. No. 11/283,483, dated Nov. 3, 2008.
Office Action from U.S. Appl. No. 11/283,483, dated Dec. 28, 2009.
Notice of Allowance from U.S. Appl. No. 11/283,484, dated Aug. 12, 2010.
Extended European Search Report from EPO Application No. 05852038.8, dated Apr. 24, 2008.
Supplemental European Search Report from EPO Application No. 05852038.8, dated May 13, 2008.
Annex to EPO Form 2001A from EPO Application No. 05852038.8, dated Aug. 1, 2008.
Examination Report from EPO Application No. 05852038.8, dated Feb. 19, 2009.
Examination Report from EPO Application No. 05852038.8, dated Jun. 23, 2009.
Examination Report from EPO Application No. 05852038.8, dated Nov. 11, 2009.
Summons to Attend Oral Hearing from EPO Application No. 05852038.8, dated May 7, 2010.
Communication EPO Application No. 05852038.8, dated Sep. 6, 2010.
Communication Pursuant to Article 94(3) EPC from EPO Application No. 05852038.8, dated Sep. 10, 2010.
Invitation to Respond to Written Opinion from Singapore Patent Application No. 200703649-4, dated Sep. 17, 2008.
Examination Report from Singapore Patent Application No. 200703649-4, dated May 19, 2009.
Examination Report from New Zealand Patent Application No. 555248, dated Oct. 8, 2008.
Examination Report from New Zealand Patent Application No. 555248, dated Nov. 25, 2009.
Examination Report from New Zealand Patent Application No. 555248, dated Dec. 7, 2009.
Examination Report from New Zealand Patent Application No. 555248, dated Jun. 2, 2010.
Examination Report from New Zealand Patent Application No. 555248, dated Jun. 10, 2010.
Office Action from Chinese Patent Application No. 200580047054.2, dated Jul. 7, 2010 with unverified English Translation.
Bellows, The Use of siRNA Screening for the Development of Novel Therapies and Mapping of Genetic Pathways, MMG 445 Basic Biotechnology eJournal 2007 3:67-72.
Denning et al., High Throughput RNAi by Reverse Transfection With Low siRNA Concentrations, Qiagen GmbH, from ePosters The Online Journal of Scientific Posters, received at the EPO on Mar. 31, 2010.
SABiosciences (Annex 2), http://sabioscience.com/RNAiInfo.iph?pcatn=SIH715685ABCD, printed Aug. 27, 2010.
Ming-Hon Hou et al., Effects of Polyamines on the Thermal Stability and Formation Kinetics of DNA Duplexes with Abnormal Structure, Nucleic Acids Research, 2001, vol. 29, No. 24 5121-5128.
Chan Yong Lee et al, Inhibitory Effect of Spermine of the Susceptibility of FNA for RNase A, Journal of the Korean Chemical Society, vol. 29, No. 6, 1985.
Super Array Bioscience's siRNA Array Plates and SureSilencing siRNA and Antibody Kits, and Ambion's Silencer Phosphodiesterase siRNA Library, Mar. 19, 2004 from http://www.genomeweb.com/rnai/superarray-biosciences-s-sirna-arr.
SABioscienes, SureSilencing siRNA Arrays, dated Jan. 1, 2009, from http://www.sabiosciences.com/RNAiArrayPlate.phr.
SABiosciences, User Manual SureSilencing siRNA Arrays, Pathway-Focused Validated Gene Knockdown by RNA Interference, Part #1029A, Version 1.1, Jan. 25, 2008.
Erfle, et al., "Reverse Transfection on Cell Arrays for High Content Screening Microscopy," Nature Protocols, vol. 2, No. 2, 2007.
Office Action dated Dec. 9, 2008 cited in U.S. Appl. No. 11/283,481.
Office Action dated Aug. 23, 2005 cited in U.S. Appl. No. 11/019,831.
Office Action dated Feb. 21, 2006 cited in U.S. Appl. No. 11/019,831.
Office Action dated Jun. 28, 2006 cited in U.S. Appl. No. 11/019,831.
Office Action dated Feb. 9, 2007 cited in U.S. Appl. No. 11/019,831.
Office Action dated Oct. 30, 2007 cited in U.S. Appl. No. 11/019,831.
Office Action dated Sep. 4, 2008 cited in U.S. Appl. No. 11/019,831.
Office Action dated Sep. 12, 2008 cited in U.S. Appl. No. 11/390,829.
Office Action dated Feb. 22, 2008 cited in U.S. Appl. No. 11/051,195.
Office Action dated Dec. 18, 2008 cited in U.S. Appl. No. 11/051,195.
Office Action dated Sep. 8, 2008 cited in U.S. Appl. No. 10/551,350.
Office Action dated Dec. 31, 2008 cited in U.S. Appl. No. 11/619,993.
Office Action dated Jan. 14, 2005 cited in U.S. Appl. No. 10/406,908.
Office Action dated Apr. 5, 2005 cited in U.S. Appl. No. 10/406,908.
Office Action dated Sep. 23, 2005 cited in U.S. Appl. No. 10/406,908.
Office Action dated Jan. 27, 2005 cited in U.S. Appl. No. 10/613,077.
Office Action dated Apr. 12, 2005 cited in U.S. Appl. No. 10/613,077.
Office Action dated Sep. 7, 2005 cited in U.S. Appl. No. 10/613,077.
Office Action dated Jul. 8, 2008 cited U.S. Appl. No. 11/283,484.
Office Action dated Nov. 3, 2008 cited U.S. Appl. No. 11/283,483.

* cited by examiner

APPARATUS AND SYSTEM HAVING DRY GENE SILENCING POOLS

CROSS-REFERENCE TO RELATED APPLICATIONS

This United States Patent Application claims benefit of U.S. Provisional Application Ser. No. 60/630,320, filed Nov. 22, 2004, and U.S. Provisional Application Ser. No. 60/678,165, filed May 4, 2005, both of which are incorporated herein by reference.

This United States Patent Application also cross-references the following U.S. patent application Ser. Nos. filed herewith: U.S. patent application Ser. No. 11/283,484 filed 18 Nov. 2005, entitled APPARATUS AND SYSTEM HAVING DRY GENE SILENCING COMPOSITIONS, with Barbara Robertson, Ph.D., et al. as inventors; U.S. patent application Ser. No. 11/283,483 filed 18 Nov. 2005, entitled APPARATUS AND SYSTEM HAVING DRY CONTROL GENE SILENCING COMPOSITIONS, with Barbara Robertson, Ph.D., et al as inventors; and U.S. patent application Ser. No. 11/283,481 filed 18 Nov. 2005, entitled METHOD OF DETERMINING A CELLULAR RESPONSE TO A BIOLOGICAL AGENT, with Barbara Robertson, Ph.D., et al. as inventors, wherein each is incorporated herein by reference.

BACKGROUND OF THE INVENTION

1. The Field of the Invention

The present invention relates to an apparatus and system for use in RNA interference. More particularly, the present invention relates to an apparatus and system that includes a well plate having a dry gene silencing composition comprised of a pool of siRNAs.

2. The Related Technology

Recently, a natural cellular regulatory pathway was discovered that uses transcribed microRNA ("miRNA") in order to control protein production. The miRNA includes a duplex region of sense and antisense RNA. This regulatory pathway uses miRNA in order to target complementary mRNA to inhibit production of the encoded protein. Accordingly, a complex series of proteins are involved in this RNA interfering pathway to inhibit or stop production of the proteins encoded by the mRNA. As such, the process is referred to as RNA interference or RNAi.

Additionally, it has been found that the RNAi pathway can be used with synthetic dsRNA (e.g., siRNA) for silencing genes and inhibiting protein expression. This can allow for siRNA having specific sequences to be produced to target complementary DNA and/or mRNA encoding a specific protein. The siRNA can interact with the natural RNAi pathway to silence a target gene and inhibit production of the encoded polypeptide. The ability to silence a specific gene and inhibit production of the encoded protein has been used for basic research of gene function, gene mapping, cellular pathway analysis, and other gene-related studies.

In order to induce gene silencing, the siRNA needs to be introduced into a cell. While the most common procedures for introducing nucleic acids into cells has been forward transfection, reverse transfection ("RTF") has been developed more recently and used as an alternative to forward transfection procedures. In certain versions of RTF protocols, a complex of lipid-nucleic acid (e.g., lipoplex) can be prepared and introduced into the test wells of a well plate. Cells are introduced into the test wells with the lipid-nucleic acid complexes, and incubated so that the siRNA can enter the cells. Examples of some RTF protocols can be found in U.S. Pat. No. 5,811,274 to Palsson, U.S. Pat. No. 5,804,431 to Palsson and U.S. Pat. No. 6,544,790 to Sabatini and in U.S. Published Applications 2002/0006664 to Sabatini and 2003/070642 to Caldwell et al. As described in these references, RTF procedures for nucleic acids generally can have fewer steps compared to traditional forward transfection and may offer benefits in attempting to isolate the transfected cells to particular regions of a single surface, such as a glass slide. However, RTF procedures for siRNA have not been optimized to the point of practical application, and improvements in gene silencing efficacy are still needed, especially for situations in which one is experimenting with multiple different siRNAs, different gene targets or different cell lines.

Therefore, it would be advantageous to have an improved RTF protocol for delivering siRNA into cells to effect gene silencing through the RNAi pathway. Additionally, it would be beneficial to have the RTF format, including the siRNA, configured in a manner that enhances the specificity of gene silencing.

BRIEF SUMMARY OF THE INVENTION

Generally, embodiments of the present invention include well plates, kits, systems, and methods of using the same for effecting gene silencing in a cell. Accordingly, the present invention provides well plates, kits, and systems that implement an improved RTF format for delivering pools of siRNAs into cells to effect gene silencing through the RNAi pathway. Additionally, the well plates, kits, and systems include siRNAs that are configured to be implemented in an RTF format in a manner that enhances the specificity of gene silencing during reverse transfection.

In one embodiment, the present invention can include a reverse transfection apparatus configured for introducing siRNAs into a cell to effect gene silencing. Such an apparatus can include a well plate having a well configured for transfecting cells. The well can include a substantially dry gene silencing composition that has at least two siRNAs which silence at least a first target gene. The gene silencing composition can be configured such that the siRNAs are each capable of being solubilized or suspended in an aqueous medium in an amount sufficient for transfecting cells in the well. Optionally, the total amount of siRNA in the well can be sufficient for implementing reverse transfection only for that well. Additionally, it is optional for the siRNAs to have at least one of a hairpin structure, modification, or a conjugate. Also, the siRNAs can be rationally designed to target the at least first target gene. Furthermore, the gene silencing composition can include a pool of siRNAs.

In one embodiment, the present invention provides a kit or system that includes a well plate consistent with any of the foregoing characterizations. Additionally, such a kit or system includes a polynucleotide carrier. The polynucleotide carrier can be a cationic lipid, polymer, lipopolymer, or the like. Additionally, the kits and systems can include various solubilizing solutions, reagents, cell culture media, and the like.

In one embodiment, the present invention includes a method of reverse transfection for introducing siRNAs into a cell to effect gene silencing. Such a method can include providing a well plate in accordance with the foregoing characterizations and includes at least two siRNAs that silence at least one target gene. An aqueous medium can be added to the well so as to suspend or solubilize each of the siRNAs into solution. Additionally, cells can be added to the well under conditions that permit the siRNA to be introduced into the cell. The cells can be added in an amount of about $1 \times 10^3$ to about 3.5×10⁴ or about 2×10³ to about 3×10⁴ cells per about 0.3 cm² to about 0.35 cm² of cell growth surface area.

In one embodiment, the method can include adding a polynucleotide carrier to the well so as to form a siRNA-carrier complex, wherein the siRNA-carrier complex can be suspended or solubilized in the aqueous medium. The siRNA-carrier complex can then contact the cell so as to initiate a sequence of events leading to the complex being internalized into the cell. As such, the polynucleotide carrier can be added as part of the aqueous medium or as an addition solution. The polynucleotide carrier can be a cationic lipid, polymer, lipopolymer, and the like.

After the cells are combined with the siRNAs, the well plate can be maintained under conditions so that cell growth, cell division, and/or gene silencing occurs. Such conditions can be considered to be standard cell culture conditions that are well known in the art. After the siRNA(s) enter the cell, the production of a target polypeptide can be silenced by at least 50%, more preferably by at least 70%, even more preferably by at least 80%, and most preferably by at least 90%.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention can be rendered by reference to specific embodiments thereof which are illustrated in the appended drawings. It is appreciated that these drawings depict only typical embodiments of the invention and are therefore not to be considered limiting of its scope. The invention can be described and explained with additional specificity and detail through the use of the accompanying drawings.

FIG. 2A depicts a DBI-siRNA walk identifying toxic siRNA, wherein the black bars represent DBI silencing, and the gray bars represent cell survival. FIG. 2B depicts cell survival resulting from the introduction of one of forty-eight eight different siRNA directed against one of twelve different targets. FIG. 2C depicts an examination of eight siRNA derived from FIG. 2B, and shows that toxicity is unrelated to target specific silencing. Also, the data demonstrates that pooling is one means of eliminating siRNA-induced toxicity. The dotted line in all of these figures represents a 75% viability cutoff.

FIG. 5A shows the GAPDH knockdown in the presence of GAPDH duplex 1, MAP2K2 duplex 1, and MAP2K1 duplex 1 (1, 1&1); and GAPDH knockdown in the presence of GAPDH duplex 2, MAP2K2 duplex 2, and MAP2K1 duplex 2 (2, 2&2); GAPDH knockdown in the presence of GAPDH duplex 4, MAP2K2 duplex 4, and MAP2K1 duplex 3 (4, 4&3); GAPDH knockdown in the presence of GAPDH duplex 5, MAP2K2 duplex 7, and MAP2K1 duplex 4 (5, 7&4); and GAPDH knockdown in the presence of GAPDH, MAP2K2, and MAP2K1 pools consisting of all of the before mentioned duplexes. FIG. 5B shows the MAP2K2 knockdown in the presence of all of the duplex combinations described in FIG. 5A. FIG. 5C shows the MAP2K1 knockdown in the presence of all the duplex combinations described in FIG. 5A.

DETAILED DESCRIPTION OF THE PREFERRED EMBODIMENTS

Figure 1A:
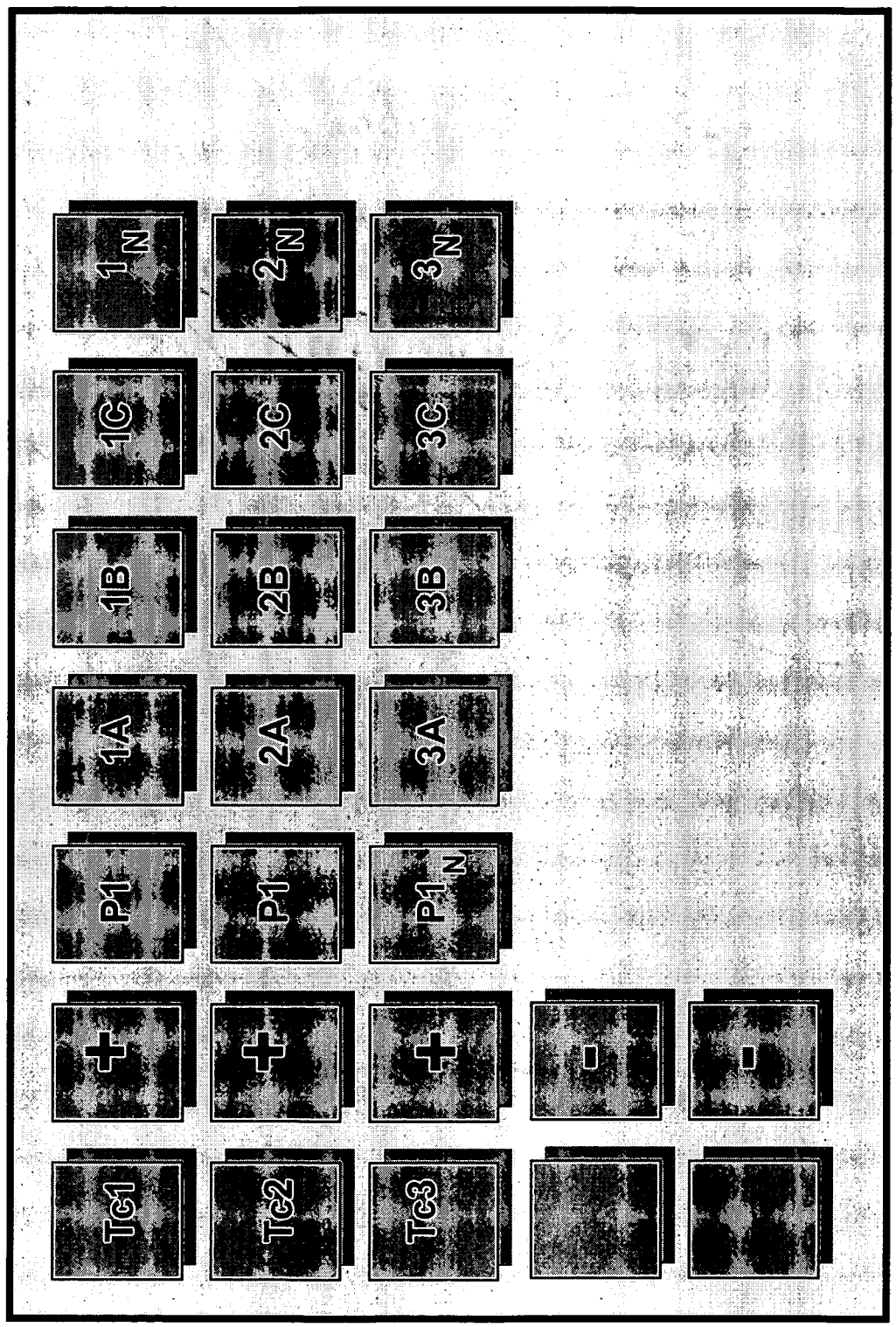
FIGS. 1A-1E are schematic diagrams that illustrate different embodiments of siRNA arrangements on a multi-well plate.

Generally, the present invention is related to an apparatus and system for use in effecting gene silencing in cells. The apparatus includes plates with wells that have dry gene silencing compositions comprised of at least two siRNAs, which can be solubilized or suspended in an aqueous medium for use in RTF protocols. The systems, which can be provided as kits, include the plates and polynucleotide carriers that can be combined with the siRNAs to form transfection complexes that are capable of entering a cell in order to deliver the siRNAs. Additionally, the system can include various other solutions and reagents for implementing RTF protocols.

The well plates, systems, kits, and methods of the present invention can be configured for use in high content screening ("HCS") applications and high throughput screening ("HTS") applications with or without the use of laboratory automation equipment. Also, the well plates, systems, kits, and methods can also be used with automated systems, such as robotic systems. However, the well plates, systems, kits, and methods can also be used in RTF protocols without the aid of automated delivery systems, or robotics, and thus can provide an efficient alternative to costly robotic delivery systems for laboratories using manual processing. Thus, the well plates, systems, kits, and methods provide versatility in choice such that high throughput screening can be done in a cost effective manner.

The following terminology is defined herein to clarify the terms used in describing embodiments of the present invention and is not intended to be limiting. As such, the following terminology is provided to supplement the understanding of such terms by one of ordinary skill in the relevant art.

As used herein, the term "2' modification" is meant to refer to a chemical modification of a nucleotide that occurs at the second position atom. As such, the 2' modification can include the conjugation of a chemical modification group to the 2' carbon of the ribose ring of a nucleotide, or a nucleotide within an oligonucleotide or polynucleotide. Thus, a 2' modification occurs at the 2' position atom of a nucleotide. Examples of a 2' modification can include a 2'-O-aliphatic, 2'-O-alkyl, 2'-O-methyl, 2'-O-ethyl, 2'-O-propyl, 2'-O-isopropyl, 2'-O-butyl, 2'-O-isobutyl, 2'-O-ethyl-O-methyl (i.e., —CH$_2$CH$_2$OCH$_3$), 2'-O-ethyl-OH (i.e., —OCH$_2$CH$_2$OH), 2'-orthoester, 2'-ACE group orthoester, 2'-halogen, and the like.

As used herein, the term "antisense strand" is meant to refer to a polynucleotide or region of a polynucleotide that is at least substantially (e.g., 80% or more) or 100% complementary to a target nucleic acid of interest. Also, the antisense strand of a dsRNA is complementary to its sense strand. An antisense strand may be comprised of a polynucleotide region that is RNA, DNA, or chimeric RNA/DNA. Additionally, any nucleotide within an antisense strand can be modified by including substituents coupled thereto, such as in a 2' modification. The antisense strand can be modified with a diverse group of small molecules and/or conjugates. For example, an antisense strand may be complementary, in whole or in part, to a molecule of messenger RNA ("mRNA"), an RNA sequence that is not mRNA including non-coding RNA (e.g., tRNA, rRNA, and the like), or a sequence of DNA that is either coding or non-coding. The antisense strand includes the antisense region of polynucleotides that are formed from two separate strands, as well as unimolecular siRNAs that are capable of forming hairpin structures with complementary base pairs. The terms "antisense strand" and "antisense region" are intended to be equivalent and are used interchangeably.

As used herein, the terms "complementary" and "complementarity" are meant to refer to the ability of polynucleotides to form base pairs with one another. Base pairs are typically formed by hydrogen bonds between nucleotide units in anti-parallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine.

Perfect complementarity or 100% complementarity refers to the situation in which each nucleotide unit of one polynucleotide strand can hydrogen bond with a nucleotide unit of an anti-parallel polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. "Substantial complementarity" refers to polynucleotide strands exhibiting 79% or greater complementarity, excluding regions of the polynucleotide strands, such as overhangs, that are selected so as to be non-complementary. Accordingly, complementarity does not consider overhangs that are selected so as not to be similar or complementary to the nucleotides on the anti-parallel strand.

As used herein, the term "conjugate" is meant to refer to a molecule, large molecule, or macromolecular structure that is coupled with either the sense strand or antisense strand of an siRNA. That is, the moiety coupled to the siRNA is considered the conjugate. For clarity purposes, the siRNA can include a conjugate that is coupled thereto by a covalent bond, ionic interaction, and like couplings. Usually, a conjugate is coupled with an siRNA in order to impart a functionality other than increasing the stabilization or targeting specificity. For examples, some conjugates, such as cholesterol, can be used to enhance the ability of the siRNA to enter a cell. Other conjugates can be labels that can be used to detect transfection or the presence of the siRNA in the cell. Usually, the conjugate is coupled to the siRNA through a linker group.

As used herein, the terms "dried" or "dry" as used in connection with gene silencing compositions is meant to refer to a composition that is not fluidic and does not flow. However, this does not exclude small amounts of water or other solvents, and includes amounts of water remaining in an RNA preparation that has equilibrated at standard or ambient conditions, for example, at one atmosphere of pressure, room temperature, and ambient humidity, such that the preparation is not in a substantially liquid form but instead is "dried" in the well. For example, an siRNA preparation is "dried" or substantially "dry" if, at about one atmosphere pressure, at about 20 to 40° C., and at about 50 to about 95% humidity, the preparation is equilibrated and, when the well plate is inverted or tilted to, for example, 90° from horizontal, the RNA preparation does not displace or flow within the well. This is in comparison to a liquid preparation which would flow or run when tilted. In various embodiments, methods for using the dry gene silencing composition in order to perform a transfection can include solubilizing or suspending the dried preparation in a suitable aqueous medium to form a mixture. Additionally, the suitable aqueous medium can include a polynucleotide carrier capable of facilitating introduction of the siRNA into a cell, and exposing the mixture to one or more cells to achieve transfection.

As used herein, the term "duplex region" is meant to refer to the region in two complementary or substantially complementary polynucleotides that form base pairs with one another, either by Watson-Crick base pairing or any other manner that allows for a stabilized duplex between the polynucleotide strands. For example, a polynucleotide strand having 21 nucleotide units can base pair with another polynucleotide of 21 nucleotide units, yet only 19 bases on each strand are complementary such that the "duplex region" has 19 base pairs. The remaining bases may, for example, exist as 5' and/or 3' overhangs. Further, within the duplex region, 100% complementarity is not required, and substantial complementarity is allowable within a duplex region. Substantial complementarity refers to 79% or greater complementarity and can result from mismatches and/or bulges. For example, a single mismatch in a duplex region consisting of 19 base pairs results in 94.7% complementarity, rendering the duplex region substantially complementary.

As used herein, the term "functionality" is meant to refer to the level of gene specific silencing induced by an siRNA. In general, functionality is expressed in terms of percentages of gene silencing. Thus, 90% silencing of a gene (e.g., F90) refers to situations in which only 10% of the normal levels of gene expression are observed. Similarly, 80% silencing of a gene (e.g., F80) refers to situations in which only 20% of the normal levels of gene expression are observed.

As used herein, the term "gene silencing" is meant to refer to a process by which the expression of a specific gene product is inhibited by being lessened, attenuated, and/or terminated. Gene silencing can take place by a variety of pathways. In one instance, gene silencing can refer to a decrease in gene product expression that results from the RNAi pathway, wherein an siRNA acts in concert with host proteins (e.g., RISC) to degrade mRNA in a sequence-dependent manner. Alternatively, gene silencing can refer to a decrease in gene product expression that results from siRNA mediated translation inhibition. In still another alternative, gene silencing can refer to a decrease in gene product expression that results from siRNA mediated transcription inhibition. The level of gene silencing can be measured by a variety of methods, which can include measurement of transcript levels by Northern Blot Analysis, B-DNA techniques, transcription-sensitive reporter constructs, expression profiling (e.g., DNA chips), and related technologies and assays. Alternatively, the level of gene silencing can be measured by assessing the level of the protein encoded by a specific gene that is translated from the corresponding mRNA. This can be accomplished by performing a number of studies including Western Blot analysis, measuring the levels of expression of a reporter protein, such as calorimetric or fluorescent properties (e.g., GFP), enzymatic activity (e.g., alkaline phosphatases), or other well known analytical procedures.

As used herein, the term "mismatch" includes a situation in which Watson-Crick base pairing does not take place between a nucleotide of a sense strand and a nucleotide of an antisense strand, where the non-base paired nucleotides are flanked by a duplex comprising base pairs in the 5' direction beginning directly after (e.g., in the 5' direction) the non-base paired nucleotides and in the 3' direction beginning directly after (e.g., in the 3' direction) the non-base paired nucleotides. An example of a mismatch would be an A across from a G, a C across from an A, a U across from a C, an A across from an A, a G across from a G, a C across from a C, and the like. Mismatches are also meant to include an abasic residue across from a nucleotide or modified nucleotide, an acyclic residue across from a nucleotide or modified nucleotide, a gap, or an unpaired loop. In its broadest sense, a mismatch as used herein includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position.

As used herein, the term "nucleotide" is meant to refer to a ribonucleotide, a deoxyribonucleotide, or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and 2'-position sugar modifications (e.g., 2' modifications). Such modifications include sugar-modified ribonucleotides in which the 2'-OH is replaced by a group such as an H, OR, R, halo, SH, SR, $NH_2$, NHR, $NR_2$, or CN, wherein R is an alkyl or aliphatic moiety. Nucleotides are well known in the art. Also, reference to a first nucleotide or nucleotide at a first position refers to the nucleotide at the 5'-most position of a duplex region, and the second nucleotide is the next nucleotide toward the 3' end. In instances the duplex region extends to the end of the siRNA, the 5' terminal nucleotide can be the first nucleotide.

As used herein, the terms "off-target" and "off-target effects" are meant to refer to any instance where an siRNA, such as a synthetic siRNA or shRNA, is directed against a given target mRNA, but causes an unintended effect by interacting either directly or indirectly with another mRNA, a DNA, a cellular protein, or other moiety in a manner that reduces non-target protein expression. Often, this can happen when an siRNA interacts with non-target mRNA that has the same or similar polynucleotide sequence as the siRNA. For example, an "off-target effect" may occur when there is a simultaneous degradation of other non-target mRNA due to partial homology or complementarity between that non-target mRNA and the sense and/or antisense strand of the siRNA.

As used herein, the term "on-target" is meant to refer to a set of modifications of an siRNA that increase the likelihood that the siRNA will preferentially target and interact with a target mRNA or DNA so as to inhibit production of the polypeptide encoded thereby. This increases the specificity of the siRNA for silencing the target gene. For example, an on-target modification can include a siRNA where the first and second nucleotide of the sense region each has a 2'-O-methyl moiety, and the antisense strand is phosphorylated at its 5' end, wherein such an on-target modification also refers to a proprietary modification coined On-Target™ (Dharmacon, Inc.). In any event, on-target modifications can be used to help reduce off-target effects. Also, an siRNA can have a sense region that has complementarity to the antisense region of the siRNA, and wherein the antisense region is the region that has complementarity to a target mRNA.

As used herein, the term "polynucleotide" is meant to refer to polymers of nucleotides linked together through internucleotide linkages. Also, a polynucleotide includes DNA, RNA, DNA/RNA, hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides. Also, polynucleotides include nucleotides with various modifications or having attachments of various entities or moieties to the nucleotide units at any position.

As used herein, the terms "rational design" and "rationally designed" are meant to refer to the selection or design of one or more siRNA(s) for use in a gene silencing application based upon one or more criteria that are independent of the target sequence. As such, rationally designed siRNA are selected to specifically interact with and inhibit polypeptide translation from a selected mRNA. Thus, for any one target mRNA there may be hundreds of potential siRNA having 18 to 31 base pairs that are 100% complementary to the target mRNA. In part, this is because a single mRNA may have multiple sequences that can be specifically targeted by the siRNA. However, it is likely that not all of the siRNA will have equal functionality. Through empirical studies, a number of other factors including the presence or absence of certain nitrogenous bases at certain positions, the relative GC content, and the like, can affect the functionality of particular siRNA. Additional information regarding rationally designed siRNA can be found in commonly owned U.S. patent application Ser. No. 10/714,333, filed on Nov. 14, 2003, related PCT application PCT/US03/36787, published on Jun. 3, 2004 as WO 2004/045543 A2, U.S. patent application Ser. No. 10/940,892, filed on Sep. 14, 2004, published as U.S. Patent Application Publication 2005/0255487, related PCT application PCT/US 04/14885, filed on May 12, 2004, and U.S. Patent Application Publication 2005/0246794, which are all incorporated herein by reference.

As used herein, the term "reverse transfection" and abbreviation "RTF" are each meant to refer to a process for introducing nucleic acid, such as an siRNA, into a cell. Such an introduction of an siRNA into a cell can be accomplished by combining the nucleic acid and cell in a well, wherein the cell has not yet been previously adhered or maintained on the growth surface. The reverse transfection proceeds by contacting the nucleic acid onto a cellular surface in a manner such that the nucleic acid can enter into the cell. Usually, the siRNA is complexed with a lipid or other polynucleotide carrier prior to being contacted to the cells. Reverse transfection differs from forward transfection because the cells have not been seeded and maintained on the cellular growth surface of a well or other container before addition of the siRNA.

As used herein, the term "sense strand" is meant to refer to a polynucleotide or region that has the same nucleotide sequence, in whole or in part, as a target nucleic acid such as a messenger RNA or a sequence of DNA. The term "sense strand" includes the sense region of a polynucleotide that forms a duplex with an antisense region of another polynucleotide. Also, a sense strand can be a first polynucleotide sequence that forms a duplex with a second polynucleotide sequence on the same unimolecular polynucleotide that includes both the first and second polynucleotide sequences. As such, a sense strand can include one portion of a unimolecular siRNA that is capable of forming hairpin structure, such as an shRNA. When a sequence is provided, by convention, unless otherwise indicated, it is the sense strand or region, and the presence of the complementary antisense strand or region is implicit. The phrases "sense strand" and "sense region" are intended to be equivalent and are used interchangeably.

As used herein, the term "siRNA" is meant to refer to a small inhibitory RNA duplex that induces gene silencing by operating within the RNA interference ("RNAi") pathway. These siRNA are dsRNA that can vary in length, and can contain varying degrees of complementarity between the antisense and sense strands, and between the antisense strand and the target sequence. Each siRNA can include between 17 and 31 base pairs, more preferably between 18 and 26 base pairs, and most preferably 19 and 21 base pairs. Some, but not all, siRNA have unpaired overhanging nucleotides on the 5' and/or 3' end of the sense strand and/or the antisense strand. Additionally, the term "siRNA" includes duplexes of two separate strands, as well as single strands that can form hairpin structures comprising a duplex region, which may be referred to as short hairpin RNA ("shRNA").

As used herein, the terms "siRNA library" or "RTF siRNA library" is meant to refer to an array of siRNAs for use in analyzing a particular biological pathway or gene target. An siRNA library comprises various siRNA pool reagents for analyzing a particular pathway or gene target. A pool typically comprises two or more non-identical siRNA directed against a single target gene. Usually, a pool includes four or more non-identical siRNA that are rationally designed. An exemplary list of siRNA libraries is provided in Table 1 below. Sequences used in certain siRNA libraries, including pool reagents, are provided in Table I and Table II of U.S. Provisional Application Ser. No. 60/678,165.

As used herein, the terms "siRNA pool," "pool," "pool of siRNAs," and "pool reagents" are meant to refer to two or more siRNA, typically four siRNA, directed against a single target gene, mRNA, and/or translation of a protein. The siRNA of the pool reagent can be rationally designed by being selected according to non-target specific criteria as described herein and in the incorporated references. For example, two nanomoles of each pool reagent can be sufficient for transfecting cells in about 200 wells of multiple 96-well plates, using 100 nM siRNA concentration. Pool reagents can be plated as a pool (i.e., the two or more siRNA of Dharmacon's SMARTpool® Reagent in a single transfection well). The individual siRNAs that comprise the SMARTpool® Reagent can also be plated individually on the same plate as the SMARTpool® Reagent.

As used herein, the term "target" is used in a variety of different forms throughout this document and is defined by the context in which it is used. The term "target gene" is meant to refer to the gene that encodes the protein to be silenced by the siRNA, and encodes for the production of the target mRNA. The term "target mRNA" is meant to refer to an mRNA against which a given siRNA is direct to silence the transcription of the polypeptide product. The term "target sequence" and "target site" are meant to refer to a sequence within the mRNA, miRNA, or DNA coding or promoter region to which the sense strand of an siRNA exhibits varying degrees of homology and the antisense strand exhibits varying degrees of complementarity. The term "target polypeptide" or "target protein" is meant to refer to the gene product encoded by the target gene, target mRNA, and/or target sequence. The term "siRNA target" can refer to the gene, mRNA, or protein against which the siRNA is directed to for silencing. Similarly, "target silencing" can refer to the state of silencing a gene, or the corresponding mRNA or protein.

As used herein, the term "transfection" is meant to refer to a process by which nucleic acids are introduced into a cell. The list of nucleic acids that can be transfected is large and includes, but is not limited to, siRNA, shRNA, sense and/or anti-sense sequences, DNA, RNA, and the like. There are multiple modes for transfecting nucleic acids into a cell including, but not limited to, electroporation, calcium phosphate delivery, DEAE-dextran delivery, lipid delivery, polymer delivery, molecular conjugate delivery (e.g., polylysine-DNA or -RNA conjugates, antibody-polypeptide conjugates, antibody-polymer conjugates, or peptide conjugates), microinjection, laser- or light-assisted microinjection, optoporation or photoporation with visible and/or nonvisible wavelengths of electromagnetic radiation, and the like. Transfections can be "forward transfections" whereby cells are first plated in wells and then treated with a nucleic acid or they can be "reverse transfections" (RTF) whereby the nucleic acid is combined with the cells before or during being plated and/or attached to the bottom of the well. Any mode of transfecting cells, such as those described above, can be used with the present invention by inducing the nucleic acid to be introduced into a cell after the siRNA is solubilized or suspended in the aqueous medium to implement reverse transfection. Details regarding a mode of reverse transfection are described in more detail below As used herein, the term "well plate" is meant to refer to a substrate that is divided into distinct regions that prevent migration from one distinct region to another distinct region, wherein the distinct regions are wells. For example, each well of a multi-well well plate may contain a horizontal well floor that may be curved or flat, as well as have sidewalls. Additionally, well plates are well known in the art.

The use of units to define measurable quantities of material, such as concentration, weight, and volume, are intended to be those that are routinely employed by those of skill in the art. Additionally, the units are preferably interpreted to correspond with the metric system. Also, the use of "u," as in "ug" or "uL" is meant to refer to "micro" as applied to microgram and microliter, respectively.

Additionally, while the foregoing term definitions are intended to supplement the knowledge of one of ordinary skill in the art, not every term within this document has been defined. As such, the undefined terms are intended to be construed with the knowledge of one of ordinary skill in the art and/or the plain meaning of the term. Additionally, the foregoing terms are not intended to be limited by the examples provided therein, but are intended to be useful in understanding and practicing the invention as described herein.

I. Reverse Transfection

Generally, the present invention provides well plates, systems, kits, and methods for implementing reverse transfection with a pool of siRNAs. The present invention provides for reverse transfection protocols with pools of siRNAs that are improved and more efficient. These improvements are particularly advantageous for manual assays as well as high throughput screenings.

In one embodiment, the present invention includes a method of reverse transfection for introducing at least one member of a pool of siRNAs into a cell to effect gene silencing. While multiple siRNAs of a pool may be introduced into a cell culture, there may be instances where only one siRNA of the pool enters a cell. Such a method can include providing a well plate that includes a well having a substantially dry gene silencing composition. The gene silencing composition can include at least two siRNAs which silence a target gene so that the production of the corresponding gene product is inhibited or stopped.

The pool of siRNAs is present in the well as part of the dry gene silencing composition so that the plates can be prepared, sealed, stored, and/or shipped long before an RTF protocol is performed. In part, this is because the dry gene silencing composition can stably retain each member of the pool of siRNAs in a functional condition within the well, and be resuspended or resolubilized with an aqueous medium during the RTF protocol. Thus, a well plate having the gene silencing composition can be manufactured and hermetically sealed in an inert environment, wherein the plate can include different wells with predefined types of siRNAs for specific gene targets, which can include individual siRNAs and pools of siRNAs. Such types of siRNAs and intended gene targets for silencing are described in more detail below.

An aqueous medium can be added to each well that contains a gene silencing composition to suspend or solubilize each of the siRNAs into the solution. The aqueous solution is allowed to solubilize the siRNAs for a sufficient duration. Optionally, the aqueous medium or an additional solution is comprised of a polynucleotide carrier. As such, a polynucleotide carrier can also be added to each well having the gene silencing composition, and the plate can be maintained for an incubation period sufficient for siRNA-carrier complexes to form. However, polynucleotide carriers are not necessary in some embodiments, and the siRNA can be transfected into the cells using other modes of transfection.

After each of the siRNAs is adequately solubilized or suspended, cells are added to the well under conditions that permit the siRNAs to be introduced into the cells. The cells can be added in an amount of about $1 \times 10^3$ to about $3.5 \times 10^4$ cells per about 0.3 cm$^2$ to about 0.35 cm$^2$ of cell growth surface area. The conditions that promote an siRNA entering a cell can be described by typical cell culture techniques used for plating cells that are well known in the art. That is, the cells can be added to the well that contains the pool of siRNAs in a manner similar to ordinary plating. The well containing the siRNAs and cells can be incubated for a duration sufficient for gene silencing to occur, which is typically less than 72 hours, more preferably less than 48 hours, and most preferably about 24 hours or less.

In one embodiment, the RTF protocol can include adding a polynucleotide carrier to the well to form an siRNA-carrier complex, wherein the siRNA-carrier complex is suspended or solubilized in the aqueous medium. After the cells are added, the siRNA-carrier complex can be contacted to the cell to induce endocytosis of the complex. The polynucleotide carrier can be added as part of the aqueous medium or in addition thereto. Thus, the polynucleotide carrier can be presented in an aqueous medium and be either solubilized or suspended therein. The polynucleotide carrier can be a lipid, cationic polymer, lipopolymer, and the like.

After the cells are combined with the siRNA, the well plate can be maintained under conditions so that cell growth, cell division, and/or gene silencing occurs. Usually, the cells are maintained in the presence of the siRNA for about 6 to about 72 hours before gene silencing is assessed, more preferably about 12 to about 36 hours, and most preferably for about 24 to about 48 hours. However, it should be recognized that the cells are incubated with the siRNA for a time period sufficient for silencing a gene so that the amount corresponding gene product decreases. As such, the production of a target polypeptide can be silenced by at least about 50%, more preferably by at least about 70%, even more preferably by at least about 80%, and most preferably by at least about 90%.

In instances where cells that grow in suspension are the target cell, such cells can be added to the wells at an appropriate cell density and plates can be spun under low gravity forces that are not detrimental to cell viability to bring the cells and lipids into close proximity on the bottom of the well.

In one embodiment, the cells transfected with the siRNAs in the RTF format can be assessed for cell viability, gene silencing, and the like. The cell viability studies can be performed in the well plate in accordance with well known procedures. Additionally, the gene silencing can also be assessed with the contents in the well by various techniques well known in the art to assess the presence or absence of target proteins. Alternatively, the amount of gene silencing can be assessed by removing the contents from the well by well known assays. In various embodiments, the well is designed to be compatible with optical detection systems such as, for example, UV, luminescence, fluorescence, or light scattering detection systems. In embodiments compatible with optical detection systems, the walls of the well can be made opaque, or rendered such that light scattering that can interfere with optical detection is reduced or minimized.

In one embodiment, the results of the RTF protocol to induce gene silencing can be detected or monitored using systems for performing high content screening ("HCS") or high throughput screening ("HTS"). An HCS analysis can be used to measure specific translocation and morphology changes, receptor trafficking, cytotoxicity, cell mobility, cell spreading, and the like. HCS studies can be performed on an ArrayScan® HCS Reader, or a KineticScan® HCS Reader (Cellomics, Inc.) Additional information on HCS can be found in U.S. Pat. Nos. 6,902,883, 6,875,578, 6,759,206, 6,716,588, 6,671,624, 6,620,591, 6,573,039, 6,416,959, 5,989,835, wherein each is incorporated herein by reference. HTS analyses can be performed using a variety of available readers, typically of the fluorescence from each well as a single measurement.

In one embodiment, the invention includes a well plate configured for having the contents of a well transferred to a location, device, or system wherein detection of the results of an siRNA RTF protocol is carried out. As such, wet transfer detection systems can be employed that include systems wherein cells are transferred from wells to a substrate such as nitrocellulose. Following the transfer of the well contents to the substrate a detection protocol can be implemented. An example of such a well plate transfer system can include nitrocellulose, wherein the well contents can be treated such that cell membranes are permeabilized or disrupted so as to gain access to intracellular contents. The transfer of the well contents to the nitrocellulose can be achieved by any suitable method including gravity or use of a vacuum manifold. The nitrocellulose containing the well contents can then be further subjected to a detection protocol that uses antibody-based detection systems and the like to detect the presence or level of one or more contents of the cells that comprise a particular well.

II. Optimizing siRNA RTF

Due to the unique and highly sensitive nature of the RNAi pathway, methodologies particularly useful for introducing pools of siRNAs into cells have been developed. Accordingly, new RTF methodologies were developed for use with pools of siRNAs. As such, recently developed protocols for implementing siRNA RTF were modified by augmenting such protocols with recently developed siRNA technologies based on rationale design, siRNA stabilization, siRNA targeting specificity, and pooling siRNAs. Thus, improved methods for implementing gene silencing with pools of siRNAs can be performed with RTF protocols ("siRNA pool RTF").

In one embodiment, the present invention may be used in connection with a diverse type of cells from a diverse set of species of the plant and animal kingdoms. Preferably, the cells are from mammalian species including cells from humans, other primates, horses, pigs, and mice. For example, cells can be HT-29 cells, LNCaP-FGC cells A549 cells, MDA-MB453 cells, HepG2 cells, THP-1 cells, miMCD-3 cells, HEK293 cells, 3T3 cells, HeLaS3 cells, MCF7 cells, Cos-7 cells, CHO-K1 cells, BxPC-3 cells, DU145 cells, Jurkat cells, PC-3 cells, Capan-1 cells, HuVEC cells, HuASMC cells, and the like. Additionally, any species of plant may be used to determine an effect of gene silencing.

The number of cells per well, which is referred to as the cell density, is an important parameter of successful siRNA pool RTF. It has been found that siRNA pool RTF protocols can have more favorable results with lower cell densities compared to RTF protocols using DNA. For example, 96-well plates can include cell densities of about 1,000-35,000 cells per well, more preferably about 2,000-30,000 cells per well, even more preferred are cell densities of about 2,500-20,000 cells per well, still more preferably about 3,000-15,000 cells per well, and most preferable are cell densities of about 3,500-10,000 cells per well. Also, the number of cells per well can be extrapolated to wells having different cell culture areas. One possible equation for calculating the appropriate number of cells that are placed in a given well is based on a 96-well plate having a cell culture area of about 0.3 cm$^2$ to about 0.35 cm$^2$, wherein well # 2 is the 96-well plate, and is described as follows:

$$\text{cells in well \#1} = \left(\frac{\text{area of well \#1}}{\text{area of well \#2}}\right) \times \text{cells in well \#2}$$

Additionally, siRNA pool RTF protocols can be optimized in order to determine whether a particular polynucleotide carrier, such as a lipid, can be useful. A first step is to test each polynucleotide carrier over a wide range of concentrations by using a robust and easily-transfected cell line (e.g., HeLa) with a well-characterized pool of siRNAs, such as a pool of positive control siRNAs, over commonly used ranges of cell density and total siRNA concentrations. Accordingly, cell viability and transfection efficacy can be assayed with the foregoing concentration gradients. Thus, optimization studies can be performed with polynucleotide carrier concentration gradients in order to determine which carriers can produce highly efficient gene silencing without inducing unfavorable cell toxicity.

In one embodiment, the present invention is directed to optimization of siRNA pool RTF protocols for implementing gene silencing through the RNAi pathway. As such, optimization of siRNA pool RTF can include any of the following: (1) selecting the type of plate; (2) selecting an appropriate solution to solubilize or suspend the siRNA for being deposited and dried in a well; (3) selecting a particular siRNA to silence specific genes; (4) identifying any modifications or conjugates that can be applied to the individual siRNA in order to enhance siRNA stability and/or specificity; (5) applying and drying the siRNA on a solid surface so that it can be solubilized or suspended in an appropriate aqueous medium; (6) selecting an appropriate mode of transfection; (7) selecting a polynucleotide carrier for siRNA such as a lipid; (8) solubilizing or suspending an siRNA; (9) complexing the siRNA with the polynucleotide carrier to form an siRNA-carrier complex; and (10) combining the siRNA-carrier complex with the cell type or types of choice. Thus, optimizing siRNA pool RTF protocols can result in a dramatic improvement over previous forward and reverse transfection procedures.

In one embodiment, the present invention can include siRNA pool RTF protocols to implement along with the foregoing optimizations, which can include any of the following: (a) applying at least two siRNA to two or more wells of a multi-well plate, wherein the pool includes siRNAs that are control siRNAs targeting a standard gene; (b) drying the pool of siRNAs on the bottom of each well; (c) adding an aqueous solution such as a media or buffer to the pool of siRNAs in each well in order to solubilize or suspend each of the siRNAs, and optionally the solution includes a polynucleotide carrier so that a siRNA-carrier complex can form; (d) adding an appropriate number of cells to each well in which the pool of siRNAs is already in solution alone or as an siRNA-carrier complex; and (e) after cells have been added, maintaining the plate under conditions in which transfection of the cells by the siRNAs can occur. Following transfection, the cells are subjected to conditions, such as liquid media, temperature, gas partial pressures, and the like, in which cell growth and/or cell division will occur and gene silencing may occur. These conditions can be, but are not necessarily, the same as the conditions under which transfection occurs, and are well known in the art.

III. Well Plates

In one embodiment, the present invention includes the use of gene silencing solutions dried in the bottom of a well in a well plate. The well plates used in connection with the present invention are preferably formatted and distinct well arrays (e.g., a 48, 96, 384, or 1536-well plate) that can be purchased from any number of commercial sources of cell culture plates and other cell culture surface-containing devices, including products such as NUNC™, NUNCLON™, MICROWELL™ and FLUORONUNC™ plates (e.g., each of which may be obtained from Nalge Nunc International of Rochester, N.Y., and Nunc A/S of Denmark), COSTAR™, COSTAR THERMOWELL™ and CORNING™ plates (e.g., each of which is available from Corning), BD FALCON™ and OPTILUX™ plates (e.g., available from Becton, Dickinson and Company) and GREINER™, CELL COAT™ and CELLSTAR™ plates (e.g., available from Greiner Bio-One).

In one embodiment, the well plate can be characterized by being configured to be suitable for cell growth and propagation. A well plate can be made of glass, polystyrene, other polymeric material or any equivalent materials, and can have rounded and/or flat well floors. However, certain analytical equipment can have enhanced functionality when using flat bottom surfaces. Additionally, wells having substantially flat floors can provide uniform cell spacing and monolayer formation. Thus, it can be preferable for the well floor to have a substantially flat bottom surface. The well floor can have a physical or chemical treatment, such as irradiation, corona discharge, plasma discharge, or microwave plasma discharge of polystyrene. Such treatments can be conventional in tissue culture surfaces upon which adherent eukaryotic cells may adhere and grow. Additionally, the wells may not be modified by any chemical coating, or they can be coated with poly-L-lysine ("PLL"), laminin, collagen, or equivalent substances that improve the adherence of cells.

Additionally, it can be preferable for each plate to have between 6 and 2000 wells, and more preferably having 1536 wells, 384 wells, or 96 wells. Also, it can be preferable for the wells to have a volume that varies between about 5 to about 2000 microliters ("uL"), and the total culture area, which is represented by the well bottom surface or cell floor, to range between about 0.02 cm² to about 4.2 cm², and about 0.3 cm² to about 0.35 cm² for a 96-well plate.

Furthermore, in some instances it can be preferably that the wells are not coated with materials such as MATRIGEL™ (Beckinson Dickerson), or are not manufactured with methods similar to those used to construct CELLBIND™ plates (Corning). In part, this is because both of these technologies are conventionally used to enhance cell attachment but have been found to reduce or diminish siRNA uptake and/or gene silencing in the RTF protocol.

IV. Gene Silencing Plates

In one embodiment of the present invention, a well plate in accordance with the foregoing can be configured to be a gene silencing plate. Accordingly, the well plate can include a gene silencing composition in one or more wells. The gene silencing composition includes at least two siRNAs that target at least a first gene for silencing. Additionally, the well plate can have a well having multiple siRNAs targeting a single gene, or multiple siRNAs targeting multiple genes. The well plates can be gene silencing plates by having an siRNA-containing solution applied to at least one well, which is then dried in a manner that removes the solution and leaves a dried gene silencing composition.

In some instances the pool of siRNAs can be solubilized in one of several types of solutions prior to applying, depositing, and/or spotting the siRNA pool solution onto the well floor, and drying the material on the plate. Usually, the siRNA pool may be dissolved in distilled water that has been treated by one of any number of art-recognized techniques to eliminate contamination by RNases such as by ultrafiltration. Alternatively, the siRNA pool may be dissolved in one of several physiologically compatible, RNase-free buffers, including but not limited to phosphate buffer, Hanks BSS, Earl's BSS, or physiological saline. These solutions may contain one or more additional reagents that enhance the stability of each of the siRNAs (e.g., RNase inhibitors) or alter the viscosity of the solution to enhance spotting or drying efficiency (e.g., sucrose) without changing the properties of any of the siRNAs or injuring the cells that are added at subsequent stages in the RTF procedure.

In still other cases, the siRNA pool may be solubilized in a medium that will enhance spotting, drying, or sticking to the plate of choice. Optionally, volatile solvents can be used that are compatible with siRNA. One example includes the use of alcohols, such as ethanol, which can be mixed with water in order to form a volatile solvent that can be readily dried and leave a dry gene silencing composition on the well floor. In some instances the solution used to deposit the siRNA pool does not contain lipids that are easily oxidized over the course of time or can be toxic to cells. In other instances the siRNAs are pre-complexed with a polynucleotide carrier before being deposited and dried to the well floor.

A predefined amount of an siRNA pool can be administered to the well so that when it is dried and then resuspended, a known amount or concentration of total or individual siRNA is available for gene silencing. The volume of siRNA pool solutions that are deposited on the bottom of each well can depend upon the concentration of the stock solution, functionality of each of the siRNAs, and desired amount or concentration of siRNAs available for gene silencing. In general, the concentration of each of the siRNAs during transfection that is needed to silence a targeted gene effectively is dependent upon the functionality of the siRNA. For this reason, the total concentration of the all the siRNAs in the pool during transfection can range from high picomolar (e.g., 300-900 pM) for highly functional siRNAs (e.g., silence>90% of target expression at 50-100 nM), to moderate nanomolar (e.g., 100 nM) for siRNAs of intermediate functionality (e.g., 70-90% silencing of target expression at 50-100 nM), and to micromolar (e.g., 1 uM) for low functionality. In general, for a 96-well plate, deposition of 5-50 uL of a 1 uM siRNA solution is sufficient to generate an acceptable concentration of siRNA pools for RTF protocols. For smaller or larger sized wells, volumes and amounts of each of the siRNAs or total siRNA can be adjusted to compensate for the final concentration of lipid-media/buffer and media that can be accommodated in each well.

In one embodiment, the total amount of siRNA in the gene silencing composition can be present in an amount for transfecting cells in only the well in which it is contained. As such, the total concentration of siRNA can be less than about 100 nM when solubilized or suspended in the aqueous medium during RTF. More preferably, the total concentration of siRNA can be less than about 50 nM when solubilized or suspended in the aqueous medium during RTF. Even more preferably the total concentration of siRNA can be less than about 25 nM when solubilized or suspended in the aqueous medium during RTF. In an additional preference, the total concentration of siRNA can be less than about 10 nM when solubilized or suspended in the aqueous medium during RTF. Most preferably, the total concentration of siRNA can be less than about 1 nM when solubilized or suspended in the aqueous medium during RTF. Additionally, the siRNA of each pool can be present in equal amounts. Alternatively, the siRNA of each pool can be present at different amounts depending on functionality, where a more functional siRNA may be present at a low concentration than a less functional siRNA. Moreover, the amount of siRNA can vary in each well. For example, the amount of siRNA in a 96-well plate can be from 0.1 picomoles ("pm") to about 100 pm, more preferably about 1 pm to about 75 pm, and most preferably about 10 pm to about 62.5 pm per well, where corresponding amounts of siRNA can be calculated for plates having other numbers of wells.

Additionally, the total amount of siRNA added to each well can be sufficient for use in a single RTF protocol within that well. That is, the pool of siRNAs in the gene silencing composition can be present in an amount to only be used with the cells added to the well. As such, the total amount of siRNAs dried in the well can be insufficient for performing two RTF protocols in two different wells. This is because the total amount of siRNA provided in the gene silencing composition is configured for a single RTF protocol in order to produce optimal results. Also, this eliminates the need to make a stock siRNA solution that is transferred into multiple wells, thereby reducing the complexity of the RTF protocol and increasing efficacy.

The siRNA-containing solutions can be deposited into wells using various well known techniques in the art for depositing liquids into wells of well plates, which can include manual and automated processes. Various methods can be used to dry the siRNA-containing solution into a gene silencing composition. In one embodiment, the plates are allowed to dry at room temperature in a sterile setting which allows the deposition solution to evaporate leaving behind the siRNA and any other conditioning compounds, such as salts, sugars, and the like. Dried plates are preferably vacuum-sealed or sealed in the presence of inert gases within a sterile container, and stored at temperatures ranging from −80° C. to 37° C. for extended periods of time without loss of silencing functionality. Thus, the plates having the substantially dry gene silencing compositions in at least one well can be stored at room temperature and shipped via traditional routes and still maintain the integrity and functionality of the siRNA.

In one embodiment, the well plate can have various other wells that can be used for control and calibration functions. As such, the well plate can have at least one well devoid or substantially devoid of siRNA. Also, the well plate can have at least one well that includes at least a first control siRNA, which can be a transfection control, positive control, or a negative control. For example, the control siRNA can include at least one of the following: (a) an siRNA that is capable of silencing a known gene; (b) transfection control siRNA; (c) an siRNA having a fluorescent marker; (d) siRNA having at least one toxic motif; (e) a non-functional siRNA; or (f) an siRNA that inhibits being taken in and processed by RISC.

V. siRNA

In one embodiment, the foregoing dry gene silencing compositions include at least two siRNAs which silences at least a first target gene. The gene silencing composition is configured such that each of the siRNAs is capable of being solubilized or suspended in an aqueous medium in an amount sufficient for transfecting cells in the well. Additionally, it is optional for the siRNAs to have at least one of a hairpin structure, modification or a conjugate. Also, the siRNAs can be rationally designed to target the gene.

In one embodiment, the pool of siRNAs is selected to optimize functionality in silencing the target gene. Preferably, the pool of siRNAs has between 50% and 100% gene silencing functionality, more preferably between 70% and 100%, even more preferably between 80% and 100%, and most preferably a gene silencing functionality between 90% and 100%. The design of functional siRNAs can be based on providing modifications that increase on-targeting, increase stability, are rationally designed for particular mRNA targets, and combinations thereof.

Additionally, each siRNA antisense strand can have varying levels of complementarity with the target sequence (e.g., mRNA). That is, the antisense strand is functional for inducing gene silencing of the target sequence. As such, the sense strand can be substantially homologous with the target sequence. Preferably, the antisense strand can have 50-100% complementarity with the target sequence. More preferably, the antisense strand can have 70-100% complementarity with the target sequence. Even more preferably, the antisense strand can have 80-100% complementarity with the target sequence. Still even more preferably, the antisense strand can have 90-100% complementarity with the target sequence. Most preferably, the antisense strand can have 100% complementarity with the target sequence.

Sequences having less than 100% complementarity can have bulges of one or more nucleotides or contain one or more mismatches. In addition, the siRNA can have overhangs of one to six nucleotides associated with the 3' and/or 5' end of the sense or antisense strands. Preferably, any overhangs are two nucleotides in length, and on the 3' end of the sense and/or antisense stands. Additionally, it should be recognized that overhangs are excluded from the calculation of complementarity, but can have homology or complementarity to the target sequence.

In one embodiment, it can be preferably to select the siRNAs from a list that have been identified from being rationally designed. As such, each of the siRNAs can be selected from Table I of incorporated U.S. Provisional Application having Ser. No. 60/678,165. Table I is entitled "siGENOME Sequences for Human siRNA," and consists of columns "Gene Name," "Accession No.," "Sequence," and "SEQ. ID NO." Table I lists about 92,448 19-mer siRNA sense strand sequences, where antisense strand sequences were omitted for clarity. The siRNA sequences listed in Table I of the includes SEQ. ID NOS. 1 to about 92,448, wherein each preferably can also include a 3' UU overhang on the sense strand and/or on the antisense strand. Each of the about 92,448 sequences of Table I can also comprise a 5' phosphate on the antisense strand. Of the about 92,448 sequences listed in Table I of the incorporated provisional application, about 19,559 have an on-targeting set of modifications. A list of sequences, identified by SEQ. ID NO., that have on-target modifications is presented in Table II, entitled "List of Table I Sequences Having On-Target Modifications Identified by SEQ. ID NO." On-target modifications are on SEQ. ID NOS. 1-22,300. The siRNA in the gene silencing compositions may be used as part of a pool.

In one embodiment, an siRNA can be configured as an shRNA having a hairpin structure with a loop region connecting a sense region with a antisense region. Also, the shRNA can have a substantially similar functionality compared to other types of siRNA. Additionally, an shRNA is not considered a modified siRNA unless the nucleotides include modifications as described in more detail below. In cases in which the siRNA is presented as a hairpin shRNA, the size and orientation of the strands can vary. Additional information regarding shRNA can be found in the incorporated reference having application Ser. No. 11/283,484, entitled APPARATUS AND SYSTEM HAVING DRY GENE SILENCING COMPOSITIONS, with Barbara Robertson, Ph.D., et al. as inventors.

In one embodiment, the present invention includes siRNA having a modification that increases specificity for gene silencing. Accordingly, specificity modifications can be incorporated into any siRNA in order to decrease off-targeting. Such specificity modifications can be an aspect of on-targeting. A more complete description of specificity modifications that reduce off-targeting can be found in the incorporated reference having application Ser. No. 11/283,484, entitled APPARATUS AND SYSTEM HAVING DRY GENE SILENCING COMPOSITIONS, with Barbara Robertson, Ph.D., et al. as inventors.

In one embodiment, the present invention includes siRNA having stability enhancing modifications. As such, the stability modifications can be use in addition or alternatively to the specificity modifications. Additionally, siRNA having stability modifications can be advantageous because they can prevent degradation by nucleases. Accordingly, the stability modifications can increase the potential shelf life of siRNA, and increase the ability to manufacture and store plates having dry gene silencing compositions for extended periods of time. A more complete description of stabilizing modifications that reduce off-targeting can be found in the incorporated reference having application Ser. No. 11/283,484, entitled APPARATUS AND SYSTEM HAVING DRY GENE SILENCING COMPOSITIONS, with Barbara Robertson, Ph.D., et al. as inventors.

For example, the pool of siRNAs can include siRNAs having modifications such as a 2'O-aliphatic (e.g., 2'-O-methyl) on the first and second nucleotides and a 5' phosphate on the antisense strand. Additionally, the modifications can include a 2'-O-aliphatic on the first and second sense nucleotides and first and/or second antisense nucleotide, and a phosphate moiety at the 5' position of the 5' terminal nucleotide of the antisense strand. A preferred modification includes a 2' modification at the first and second sense nucleotides and at the second antisense nucleotide, and a phosphate on the antisense 5' terminal nucleotide.

In one embodiment of the present invention, the siRNA can include a conjugate coupled to the sense and/or antisense strands. The conjugate can perform a variety of functions or provide additional functionalities to the siRNA. For example, the conjugate can increase the penetration of the siRNA through a cell membrane with or without being complexed with a carrier. Additionally, the conjugates can be labels that can be monitored or identified in order to determine whether or not a labeled siRNA entered a cell. A complete description of conjugates that can be coupled to siRNA can be found in the incorporated reference having application Ser. No. 11/283,484, entitled APPARATUS AND SYSTEM HAVING DRY GENE SILENCING COMPOSITIONS, with Barbara Robertson, Ph.D., et al. as inventors.

VI. Pools of siRNA

Off-targeting occurs when an siRNA designed to target and silence one gene unintentionally targets and silences one or more additional genes. Such off-targeting can occur due to varying levels of complementarity between the sense and/or antisense strand of the siRNA and the unintended target mRNA. The consequences that arise from off-targeting can include the silencing of critical genes, and can give rise to a variety of phenotypes (e.g., cell death, cell differentiation). Also, off-targeting can generate false positives in various phenotypic screens. As such, the consequences of off-targeting represent a challenging obstacle to the implementation of large scale, genome-wide siRNA-based phenotypic screens. Accordingly, it is advantageous to reduce and eliminate any off-target gene silencing. Off-targeting can be reduced by using a pool of siRNAs.

In one embodiment, the consequences of off-targeting can be minimized or inhibited by using a pool of siRNAs. Pools of siRNAs have been shown to generate fewer off-target effects as compared to single siRNA. As noted above, the pools may comprise two or more siRNAs that are substantially complementary to different subsequences of one target mRNA or they may be substantially complementary to subsequences of different target mRNAs. For example, a first siRNA and a second siRNA can contain antisense sequences that are substantially complementary to first and second subsequences of one target mRNA. The first and second subsequences can be mutually exclusive or overlapping. Accordingly, the individual siRNAs in a pool can be directed to various portions of the gene encoding the protein to be silenced. The gene silencing composition can include pools that have two, three, four, five, or more different siRNAs. The benefit of reducing off-target effects due to a pool of siRNAs is particularly noticeable when at least two siRNAs are directed against the same target. The benefits of using pools of siRNA are described in U.S. patent application Ser. No. 10/714,333, filed Nov. 14, 2003, related PCT application PCT/US03/36787, published on Jun. 3, 2004 as WO 2004/045543 A2, U.S. patent application Ser. No. 10/940,892 filed Sep. 14, 2004, published as U.S. Patent Application Publication 2005/0255487, and U.S. Patent Application Publication 2005/0246794, wherein each is incorporated herein by reference.

Accordingly, the increased number of siRNAs in a pool that are directed against a particular target can increase the likelihood that at least one siRNA with satisfactory functionality will be included. Also, a pool of siRNAs can provide a benefit from additive or synergistic effects. Further, two or more siRNAs directed against a single gene that do not have satisfactory levels of functionality alone can be combined in order to silence the target gene and inhibit production of the encoded protein with increased efficacy. Additionally, multiple siRNAs in a pool that target a single gene can increase the probability of gene silencing, and improve the overall economics of implementing gene silencing when compared to adding different siRNAs sequentially. This effect is contrary to the conventional wisdom that the concurrent use of multiple siRNA will negatively impact gene silencing.

The reduction of off-targeting or increased specificity can also be achieved by using pools with individual siRNA concentrations that are below the level that induces off-target effects. As an example, transfection of a single siRNA at 100 nM can induce 90% silencing, yet the high concentration of the siRNA also induces off-target effects. In contrast, a pool of four siRNAs (e.g., total concentration of 100 nM, 25 nM each) can similarly induce 90% silencing. Since each siRNA is at a four-fold lower concentration, the total number of off-targets is fewer. Thus, in order to obtain silencing with inhibited or no off-target effects, a highly functional siRNA can be used at low concentrations, and/or pools of siRNA targeting the same gene can be used with each siRNA of the pool having a concentration that is sufficiently low to minimize off-target effects.

Additionally, rationally designed pools of siRNA can be configured to include different siRNA at uneven concentrations. For example, a first siRNA in the pool can be present at 10% of the total siRNA, the second at 30% of the total, the third at 40% of the total, and the fourth at 20% of the total siRNA in the pool. This can be implemented to include highly functional siRNA with high off-targeting at lower concentrations and less functional siRNA with less off-targeting at higher concentrations.

The pools of siRNA can be used with siRNA that are modified or unmodified. Such modifications can be employed to increase specificity, increase stability, increase on-targeting, decrease off-targeting, and combinations thereof. It is preferred that the pools include at least one modified siRNA, and it is most preferably that the modified siRNA includes an on-targeting or specificity enhancing modification.

VII. Polynucleotide Carriers

In one embodiment, the present invention includes polynucleotide carriers that can interact with each siRNA in a pool, and transport the siRNA across a cell membrane. However, in other embodiments of the invention modes of transfection can be implemented without carriers, such as by electrophoresis, precipitation, particle bombardment, optoporation, and microinjection. Usually, polynucleotide carriers include a positive charge that interacts with the negatively charged phosphates on the polynucleotide backbone. Polynucleotide carriers are well known in the art of cellular nucleic acid delivery. Preferred polynucleotide carriers include cationic polymers, lipids, lipopolymers, lipid-peptide mixtures, and the like that are capable of complexing with an siRNA and delivering the siRNA into a cell in a manner that retains the gene silencing functionality without being overly toxic. As such, routine experimentation can be implemented with procedures described herein with respect to optimizing RTF in order to identify the optimal polynucleotide carrier for a certain system or cell.

In one embodiment, lipids or lipid-peptide mixtures are preferable for introducing a pool of siRNAs into a target cell. Typically, the lipid is a cationic lipid. Cationic lipids that can be used to introduce siRNAs into cells can be characterized by having little or no toxicity (e.g., defined as less than 15-20% toxicity), which can be measured by AlamarBlue or equivalent cell viability assays. Additionally, the lipids can deliver sufficient amounts of siRNA into cells in order to induce gene silencing. However, not all lipids are functionally equivalent and certain lipids can perform better with specific cell lines. Thus, the foregoing optimization procedures can be employed to determine an appropriate lipid and lipid concentration for delivering a pool of siRNAs for a specific cell line. Peptides that have affinity to one or more proteins, lipids, lipid-polysaccharide, or other components of the cell membrane can be conjugated to the siRNA and used independent of lipids or advantageously combined with one or more lipids to form a polynucleotide carrier. Such lipid-peptide mixtures can enhance RTF of siRNA. Cholesterol conjugates can be similarly coupled to the siRNA and be used independent of polynucleotide carriers or advantageously combined therewith.

Briefly, in order to identify whether a given lipid is acceptable for siRNA pool RTF, two or more well characterized siRNAs can be tested under a variety of lipid, media, and siRNA concentrations using the optimizing RTF protocols described herein. Subsequently, the level of silencing of the targeted gene and the level of cell death are quantified using art-accepted techniques. Suitable lipids for siRNA pool RTF include OLIGOFECTAMINE™, TransIT-TKO™, or TBIO Lipid 6™, LIPOFECTAMINE™ 2000, lipids DharmaFECT™ 1, DharmaFECT™ 2, DharmaFECT™ 3, and DharmaFECT™ 4 (Dharmacon, Inc.). The term "DharmaFECT™" (followed by any of the numerals 1, 2, 3, or 4) or the phrase "DharmaECT™ transfection reagent," refers to one or more lipid-based transfection reagents that have been optimized to transfect siRNA rather than larger nucleic acids (e.g., plasmids). Additional information on lipids can be obtained in U.S. Pat. Nos. 5,674,108, 5,834,439, 6,110,916, 6,399,663, and 6,716,582, and international publications WO 00/12454 and WO 97/42819.

The formation of a functional siRNA-lipid complex can be prepared by combining a pool of siRNAs and the lipid. As such, an appropriate volume of lipid at a selected concentration can be combined with a volume of media and/or buffer to form a lipid-media or lipid-buffer having a suitable concentration of lipid. For example, a volume of lipid media ranging from about 5-50 microliters ("uL") can include about 0.03-2 micrograms ("ug") of lipid to be introduced into each well of a 96-well plate, and the amount of lipid can be changed to correspond with other well sizes. The choice of media and/or buffer for siRNA pool RTF can improve the efficiency of the RTF protocol. Some media contain one or more additives that induce cell toxicity and/or non-specific gene modulation during RTF. Examples of preferred media or buffers include Opti-MEM™ (GIBCO, Cat. # 31985-070), HyQ-MEM-RS™ (HyClone, Cat.# SH30564.01), Hanks Balanced Salt Solution™, or equivalent media. A suitable media can be identified by employing the optimization protocol described herein.

The lipid-media or lipid-buffer can be introduced into a well by a variety of methods including hand-held single and multi-channel pipettes, or more advanced and automated delivery systems that can inject measured volumes of the lipid solution into a well. The lipid solution can be incubated in the well that contains the dried gene silencing composition for a period of time that is sufficient to solubilize or suspend the siRNAs, and to form siRNA-lipid complexes (e.g., lipoplexes). In general, the process of siRNA solubilization and lipoplex formation can require about 20 minutes, but usually not more than 120 minutes. The complex formation process is generally performed at room temperature, but can be performed at temperatures ranging from 4-37° C. In some instances, the lipid and siRNAs can be mixed by agitating the plate (e.g., swirl, vortex, sonicate) for brief periods (e.g., seconds—minutes) to enhance the rate of siRNA solubilization and complex formation.

Additionally, any of the foregoing polynucleotide carriers can be included in systems or kits in accordance with the present invention. Such kits can include the plates having a gene silencing composition with a pool of siRNAs, and can be distributed with siRNA solubilizing or suspending solutions, polynucleotide carriers, carrier solutions, reagents, cell media, and the like.

VIII. Well Arrangements

In one embodiment, the siRNA pool RTF plates that include multiple wells having different dry gene silencing compositions can have the wells organized into predefined arrangements. Such arrangements can correspond to the type of assay being employed with the siRNA pool RTF plate. That is, when a family of genes is being studied, the pools of siRNAs that target the same gene can be organized in one column or row while the pools of siRNAs targeting a different gene can be organized in a different column or row. Thus, the wells can be organized into a pre-selected arrangement so that particular siRNAs are in a pre-selected pattern on a plate. The pre-selected pattern can include control wells, such as those that include one or more negative and/or positive siRNA controls, and transfection controls. Also, the pre-selected pattern can include wells that are empty or substantially devoid of siRNA, which can be used as controls and for calibrations.

It can be beneficial to have pools of siRNAs that are pre-dried in corresponding wells of different well plates so that multiple plates can be prepared simultaneously. This can allow for well plates to have gene silencing compositions at standardized positions and amounts of siRNAs, which is beneficial for using standardized well plates in multiple experiments that can be conducted over time without introducing variability between the plates. The use of standardized plate arrangements can provide a series of plates that can be used over time and provide data that can be analyzed together.

For example, a plate comprising a plurality of columns of wells can include a transfection control in the first column, positive controls for RNAi in the second column, negative controls for RNAi in a third column, a pool of siRNA directed against a single target in a fourth column, and individual members of the siRNA pool that comprise the fourth column are in subsequent columns, such as the fifth through twelfth columns. Alternatively, the fifth through twelfth columns can comprise different concentrations of each siRNA in the pool of column four, with the amount of siRNA increasing from well to well or decreasing from well to well. Each well can include one concentration of each siRNA in the pool, or two, three, four, five, or more concentrations of each siRNA in the pool can be in different wells. Alternatively, the same pool of siRNA can be varied from well to well at a gradient of concentrations. The number of concentrations of individual siRNA or pools of siRNA that can be used is limited only by the number of wells on the plate; however, multiple plates can be configured to be used together with a predefined pattern that spreads across all the plates.

Accordingly, the pre-selected patterns of siRNA concentration gradients can be used as a pattern that can be observed so that the optimal amount of each siRNA in a pool can be determined by observing the level of silencing by a particular siRNA at a number of concentrations. For example, sequential rows in the fourth column can have sequentially increasing or decreasing amounts of total pool siRNA. Additionally, sequential columns can include sequentially increasing or decreasing amounts of individual siRNA of the pool.

Figure 1B:
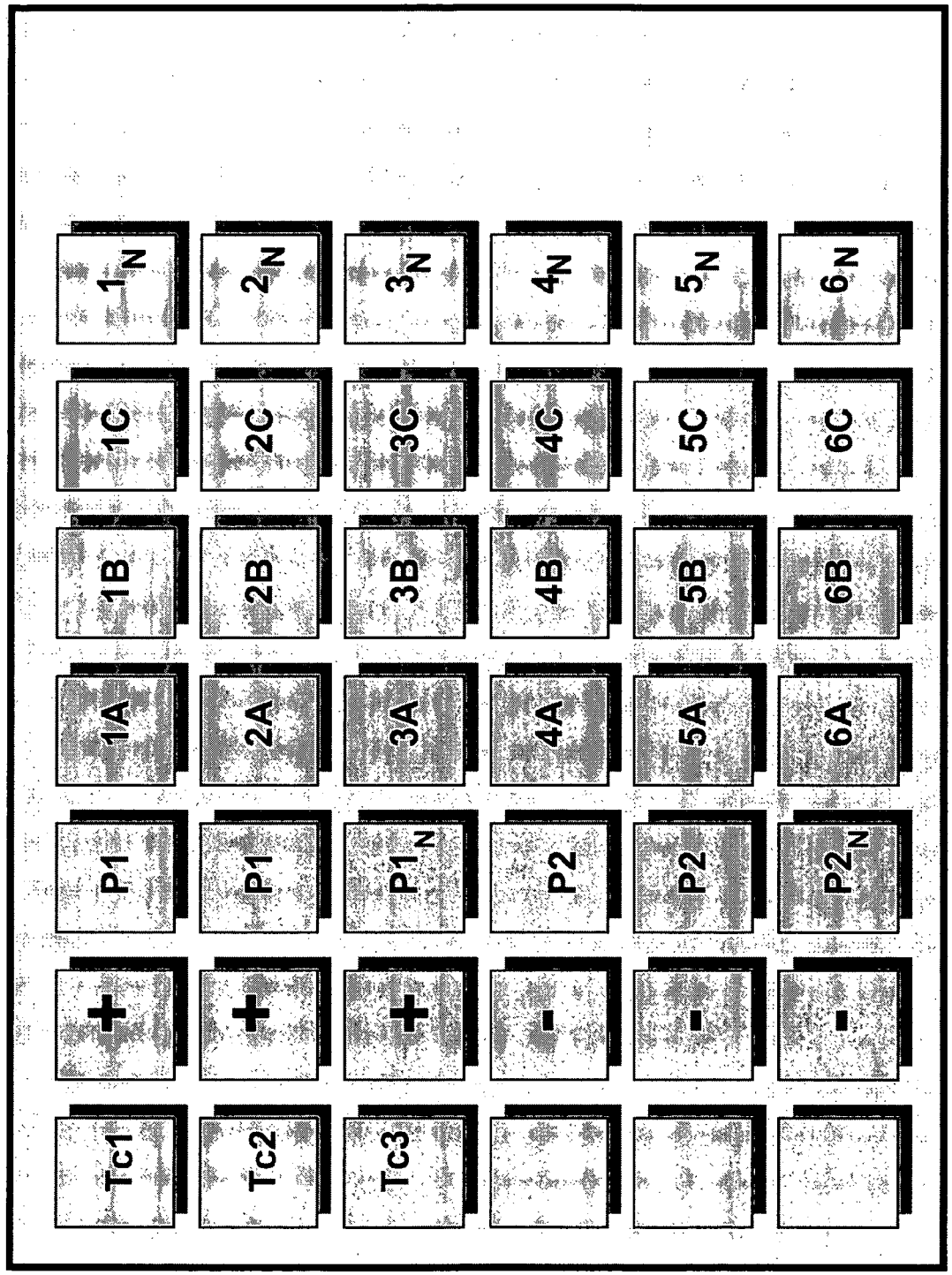

FIGS. 1A and 1B illustrate embodiments of plate arrangements similar with the foregoing concentrations arrangements. While the wells are shown to be square, it should be recognized that they can be any shape. Also, the well plate can include any number of wells, and the number of wells depicted is merely for example. In the figures the wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" through "P1$_N$" indicate a first pool which silences a first gene at a concentration gradient; "P2" through "P2$_N$" indicate a second pool which silences a second gene at a concentration gradient; "1A" through "1$_N$" indicate a first individual siRNA of the first pool at a concentration gradient; "2A" through "2$_N$" indicate a second individual siRNA of the first pool at a concentration gradient; "3A" through "3$_N$" indicate a third individual siRNA of the first pool at a concentration gradient; "4A" through "4$_N$" indicate a first individual siRNA of the second pool at a concentration gradient; "5A" through "5$_N$" indicate a second individual siRNA of the second pool at a concentration gradient; and "6A" through "6$_N$" indicate a third individual siRNA of the second pool at a concentration gradient. Thus, FIG. 1A illustrates a well plate assaying a single pool, and FIG. 1B illustrates a well plate assaying multiple pools. Additionally, a well plate can include more than two pools. Also, the pools and single siRNA can be rationally designed, and/or have modifications or conjugates.

Figure 1C:
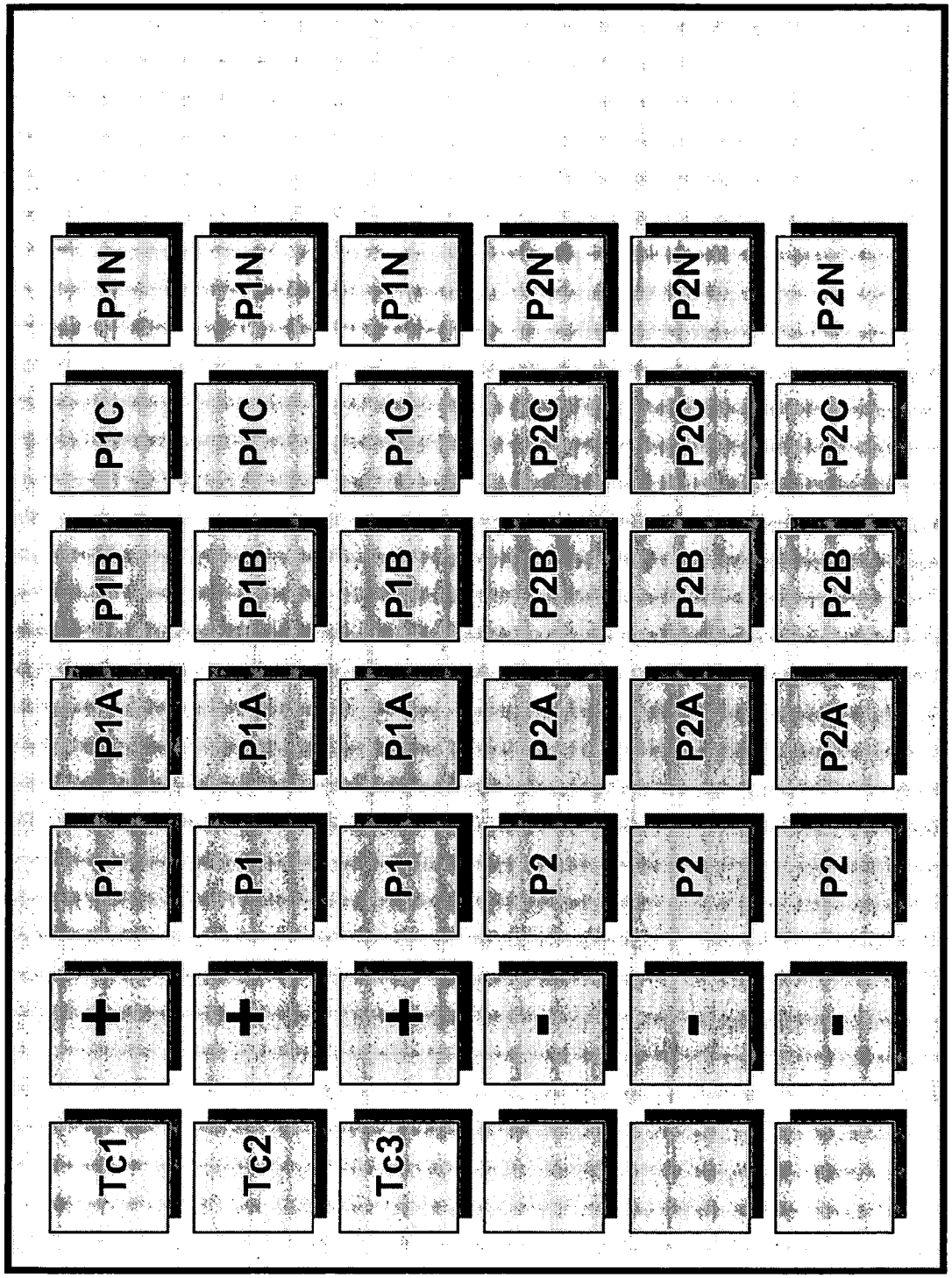

FIG. 1C illustrates another embodiment of a plate arrangement similar with the foregoing concentrations arrangements. The wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" indicates a first pool in triplicate which silences a first gene at a standard concentration; "P1A" through "P1N" indicates the first pool at a concentration gradient A-N, each in triplicate; "P2" indicates a second pool in triplicate which silences a second gene at a standard concentration; and "P2A" through "P2N" indicate the second pool at a concentration gradient A-N, each in triplicate. Accordingly, multiple wells can be used to test each gene silencing composition and/or condition.

Figure 1D:
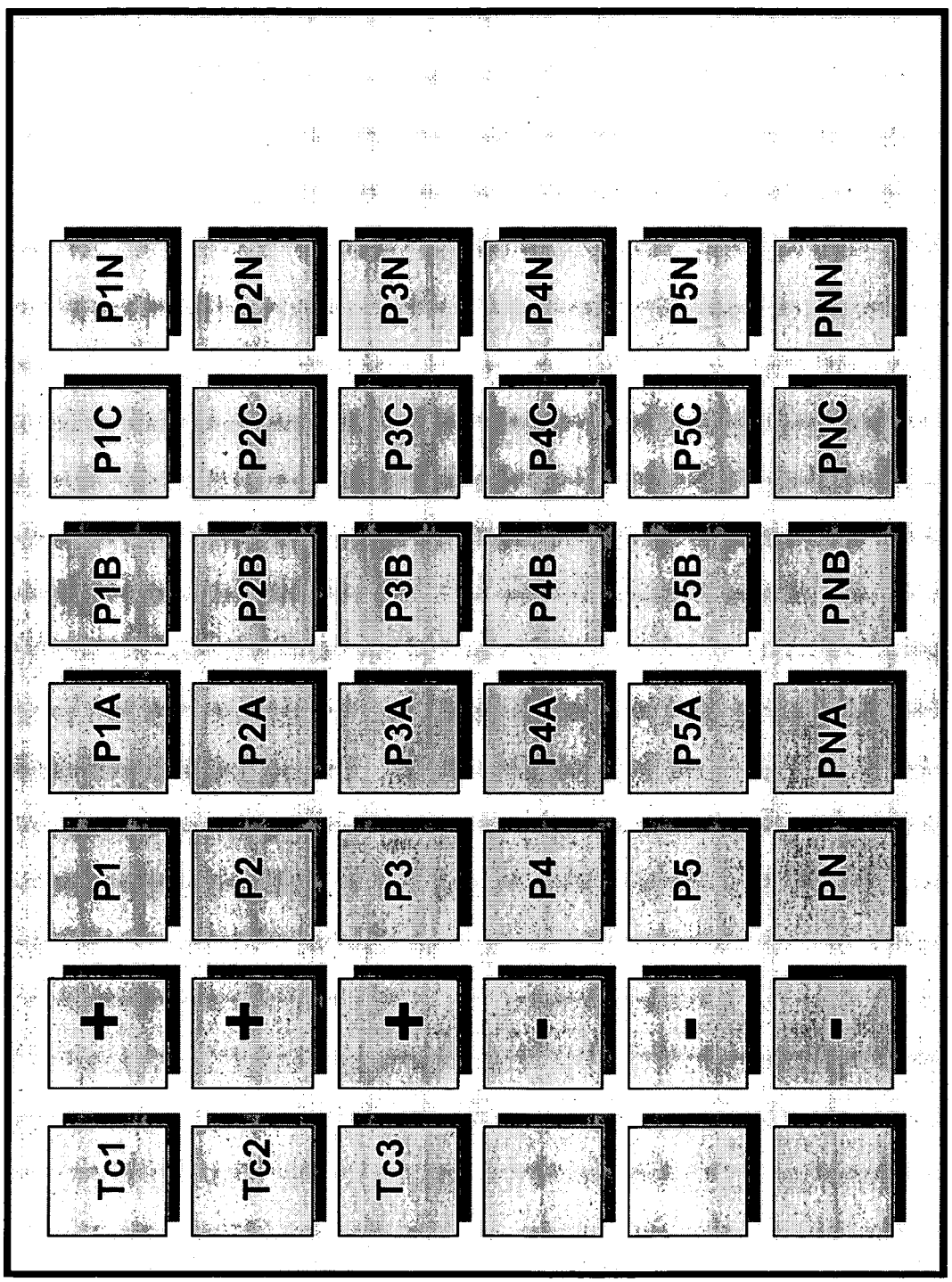

FIG. 1D illustrates an embodiment of a plate arrangement similar with the foregoing concentrations arrangements. The wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" through "PN" indicate a first pool which silences a first gene through an N$^{th}$ pool which silence an Nth gene at a standard concentration; and "P1A" through "P1N" indicate the first pool at a concentration gradient A-N, wherein second pool (e.g., "P2A"-"P2N") through N$^{th}$ pool (e.g., "PNA"-"PNN") each have a similar concentration gradient. Thus, multiple pools can be studied at different concentrations, wherein the multiple pools can be related or different.

Figure 1E:
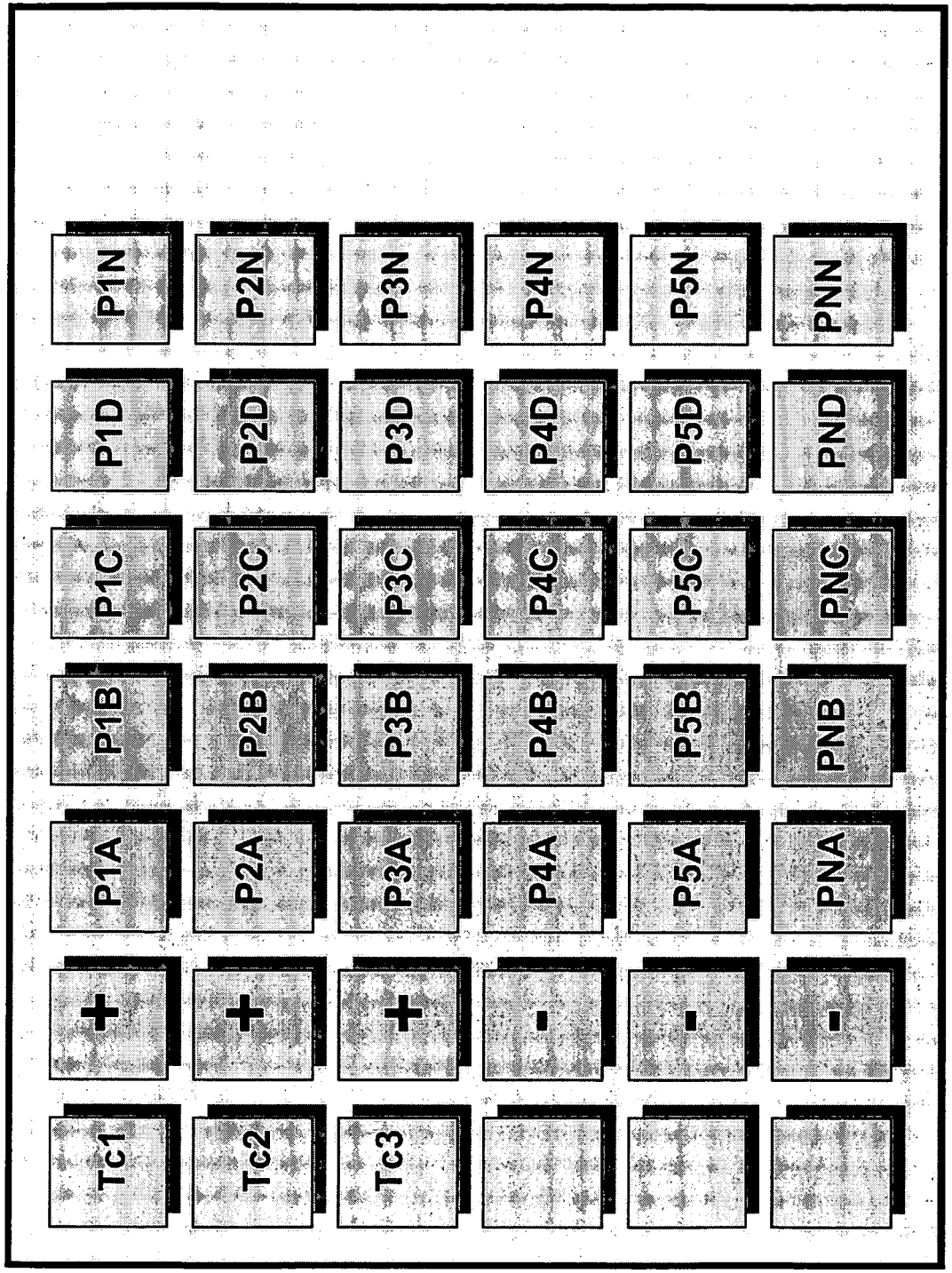

FIG. 1E illustrates an embodiment of a plate arrangement similar with the foregoing concentrations arrangements. The wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1A" is a first pool that silences a first gene; "P1B" is a second pool that silences the first gene; "P1C" is a third pool that silences the first gene; "P1D" is a fourth pool that silences the first gene; "P1N" is an N$^{th}$ pool that silences the first gene; "P2A" through "PNA" indicate a second through N$^{th}$ pools that silence related second through N$^{th}$ genes; and the corresponding wells in each of the "P2A" through "PNA" rows are A-N pools which silences the gene of the row. Thus, plates can be arranged with multiple pools targeting multiple related genes for silencing.

Additionally, a well plate can be arrainged to include a number of different siRNAs that are modified and/or unmodified in different wells. For example, a 96-well plate may contain the following: 10-12 wells of first pool of siRNAs that are unmodified; 10-12 wells of the first pool of siRNAs that are modified; 10-12 wells of a second pool of siRNAs that are unmodified; 10-12 wells of the second pool of siRNAs that are modified; 10-12 wells of a third pool of siRNAs that are unmodified; 10-12 wells of the third pool of siRNAs that are modified; 10-12 wells of a fourth pool of siRNAs that are unmodified; and 10-12 wells of the fourth pool of siRNAs that are modified. The individual siRNAs of the first, second, third and fourth pools of siRNAs may be directed to different regions of the same target mRNA such that may or may not overlap, or they may be directed to different mRNA that code for unrelated proteins, or proteins that have similar functions or act in the same biological pathway. Also, multiple pools can contain the same siRNA, but also include additional different siRNAs so that the combination of each pool is different from the other pools.

In another embodiment, a well plate can be arranged so that some of the wells comprise pools, and some of the wells comprise single types of siRNA. Thus, the well plate may have different wells that comprise the following: (i) a first siRNA, a second siRNA, a third siRNA, a fourth siRNA, and a fifth siRNA, any of which may be modified or unmodified; (ii) the first siRNA, the second siRNA, the third siRNA, and the fourth siRNA, any of which may be modified or unmodified; (iii) the first siRNA, the second siRNA, the third siRNA, and the fifth siRNA, any of which may be modified or unmodified; (iv) the first siRNA, the second siRNA, the fourth siRNA, and the fifth siRNA, any of which may be modified or unmodified; (v) the first siRNA, the third siRNA, the fourth siRNA, and the fifth siRNA, any of which may be modified or unmodified; (vi) the second siRNA, the third siRNA, the fourth siRNA, and the fifth siRNA, any of which may be modified or unmodified; (vii) the fifth siRNA, which may be modified or unmodified; (vii) a sixth siRNA, which may be modified or unmodified; (viii) a seventh siRNA, which may be modified or unmodified; (ix) an eighth siRNA, which may be modified or unmodified; (x) a ninth siRNA, which may be modified or unmodified; and/or (xi) a control siRNA.

In one embodiment, libraries of pools of siRNAs can be provided in an array format for use in siRNA pool RTF protocols, wherein at least some of the siRNAs are present in pools of siRNAs. Preferably, the array comprises an siAR-RAY® RTF siRNA Library (Dharmacon, Inc.). An RTF siRNA library can be present in a well plate as different gene silencing compositions in an array pattern so as to form a gene silencing composition array. The gene silencing composition array can be used to study entire gene families or regulatory pathways with individual and/or pools of siRNA. These gene silencing composition arrays or siRNA libraries can contain pre-selected groups of rationally designed pools of siRNA, such as Dharmacon's SMARTpool® siRNA reagents. These pools of siRNA can target genes confirmed to be relevant to a particular pathway or to be phylogenetically related to the indicated gene family.

In one embodiment, each pool of siRNAs (e.g., SMARTpool® reagent) can designed with Dharmacon, Inc.'s multi-component, proprietary SMARTselection™ algorithm. The reagents can be deposited and dried in well of a well plate in triplicate and can be used for a single transfection into the cell type of interest for rapid screening of the siRNA library.

For example, at least one well plate can include an RTF siRNA library, wherein each plate has a maximum of 80 wells having rationally designed siRNA, such as SMARTpool® siRNA reagents. Each gene silencing composition can include the rationally designed siRNAs at about 6.25 pmol of total siRNA per about 0.3 cm$^2$ to about 0.35 cm$^2$ cell culture area or well floor. As such, the amount of each individual siRNA in each pool is about 1.56 pmol about 0.3 cm$^2$ to about 0.35 cm$^2$ per cell culture area or well floor. The gene silencing compositions are presented in a matrix format, wherein each SMARTpool® siRNA reagent contains four different siRNA duplexes targeting a single gene. Such a well plate can be prepared as a kit that includes a DharmaFECT™ transfection reagent supplied as a liquid at a concentration of 1 ug/uL. The kit preferably also comprises DharmaFECT™ Cell Culture Reagent supplied as a liquid.

Additionally, the well plate arrangements can be organized in order to study libraries of siRNAs, which can be provided in an array format using pools of siRNAs. Preferably, the array comprises an RTF siRNA library. An RTF siRNA library can be used to study entire gene families or regulatory pathways. These siRNA libraries contain pre-selected groups of rationally designed pools of siRNA reagents targeting genes confirmed to be relevant to a particular pathway or to be phylogenetically related to the indicated gene family. Additionally, examples of such siRNA libraries can be reviewed in Table 1.

TABLE 1

SIRNA LIBRARIES

| Plate(s)/Pathway | Number of Genes |
| --- | --- |
| Human Genome | ~22,000 |
| Human Druggable Set | 7309 |
| Protein Kinases | 779 |
| Tyrosine Kinases | 85 |
| Calcium/Calmodulin Protein Kinase (CaMK) | 71 |
| CMGC Kinases | 60 |
| AGC Kinases | 59 |
| Mitogen-Activated Protein Kinase (MAPK) | 58 |
| S-T Kinases | 54 |
| Proteases | 514 |
| Serine Proteases | 128 |
| Metallo Proteases | 128 |
| Cysteine Proteases | 74 |
| G-Protein Coupled Receptors | 518 |
| Apoptosis | 318 |
| Ion Channels | 286 |
| Phosphatases | 193 |
| Cytokine Receptors | 166 |
| Membrane Trafficking/Remodeling | 122 |
| Cell Cycle Regulation | 111 |
| Deubiquinating Enzyme | 106 |
| Undifferentiated Cancer | 69 |
| Neoplastic Tissue | 67 |
| Nuclear Receptor | 49 |
| Insulin Signaling Pathway | 31 |
| Protein Hydroxylase | 24 |

Descriptions of siRNAs comprising the siRNA libraries in Table 1, and more complete descriptions of the use of gene silencing to study the plates/pathways identified in Table 1 are provided in U.S. Provisional Application Ser. No. 60/678, 165. Moreover additional descriptions of plate arrangements and the types of genes that can be studied using pools of siRNA are provided in U.S. Provisional Application Ser. No. 60/678,165

EXAMPLES

The following examples are provided to describe some embodiments of the present invention in a manner that can be use by one of skill in the art to practice the present invention. Additionally, the following examples include experiments that were actually performed as well as prophetic experiments. Additional examples and supplementary information for the following examples can be reviewed in the incorporated references having application Ser. No. 11/283,484, entitled APPARATUS AND SYSTEM HAVING DRY GENE SILENCING COMPOSITIONS, with Barbara Robertson, Ph.D., et al. as inventors, application Ser. No. 11/283, 484, entitled APPARATUS AND SYSTEM HAVING DRY CONTROL GENE SILENCING COMPOSITIONS, with Barbara Robertson, Ph.D., et al. as inventors, and U.S. Provisional Application Ser. No. 60/678,165. The polynucleotide sequences that were used in the examples can be found in Tables I-IV of U.S. Provisional Application Ser. No. 60/678, 165, and the sequence listing of the reference having application Ser. No. 11/283,484, entitled APPARATUS AND SYSTEM HAVING DRY GENE SILENCING COMPOSITIONS, with Barbara Robertson, Ph.D., et al. as inventors.

Example 1

A series of studies were conducted to asses the ability of certain siRNA sequences to have toxic effects, to assess whether off-targeting causes toxicity, and whether off-targeting can be minimized using pools of siRNA. Accordingly, a population of randomly selected siRNAs derived from a walk targeting DBI (e.g., NM_020548, position 202-291) was assessed for the ability of certain siRNA sequences to induce toxicity. The collection of siRNAs consisted of 90 individual (e.g., 19 bp) duplexes, and covered the respective regions in single base steps. Duplexes were forward transfected into HeLa cells using LIPOFECTAMINE™ 2000, and a threshold of 75% cell viability was used as the cutoff to distinguish toxic from nontoxic sequences.

Figure 2A:
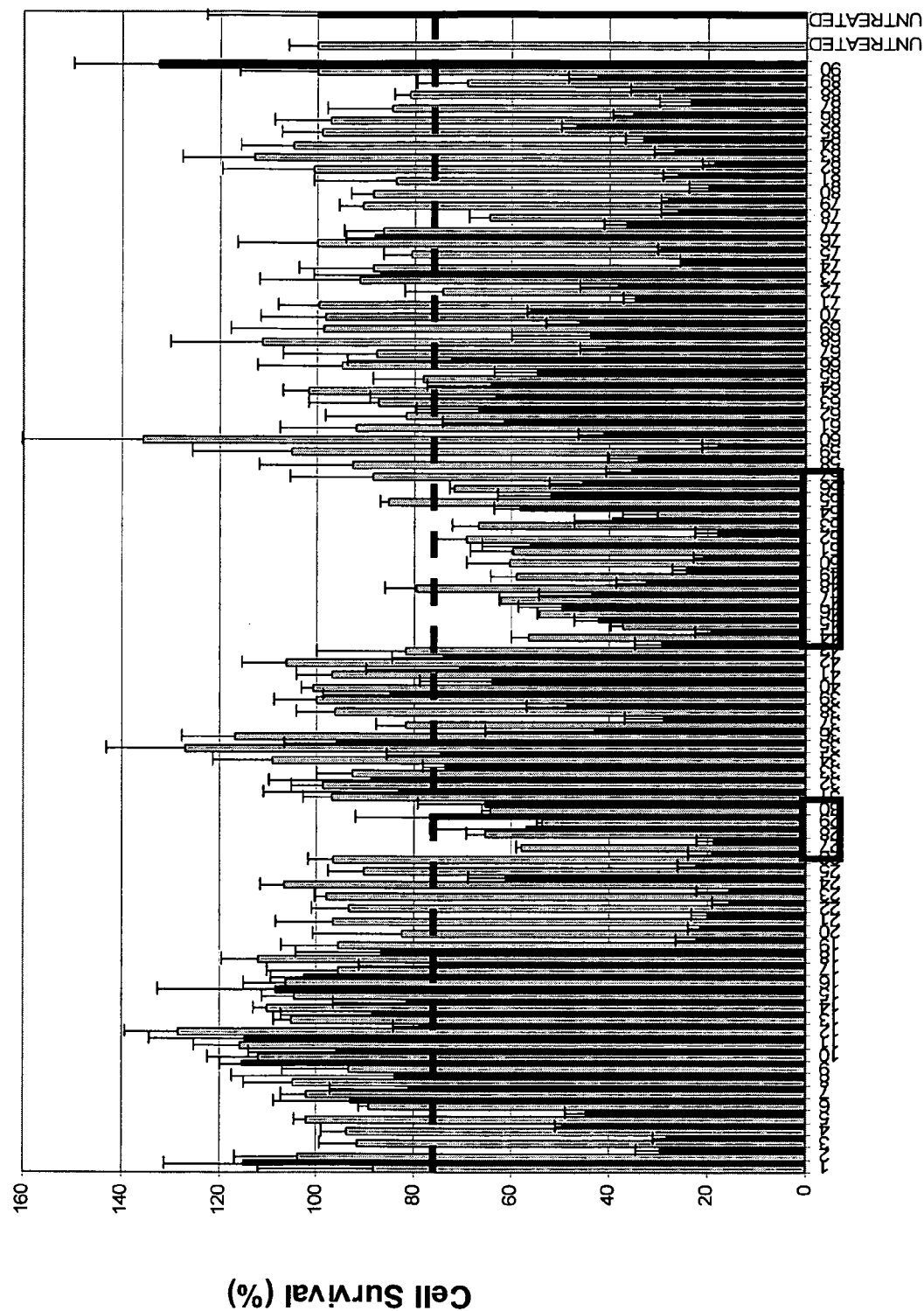
FIGS. 2A-2C are graphical representations of an embodiment of the identification of toxic siRNA. HeLa cells were forward transfected at 5,000 cells per well with 10 nM siRNA.

FIG. 2A is a graphical representation of the results of the toxicity study. As shown, the siRNAs transfected under these conditions were observed to induce varying levels of cellular toxicity. Overall, 14 out of 90 siRNA duplexes (e.g., 15.5%) were found to decrease cellular viability below 75%, which is identified by the horizontal dashed line. These toxic siRNA can be identified by the numbers within the boxes that show cell survival below the dashed line.

Figure 2B:
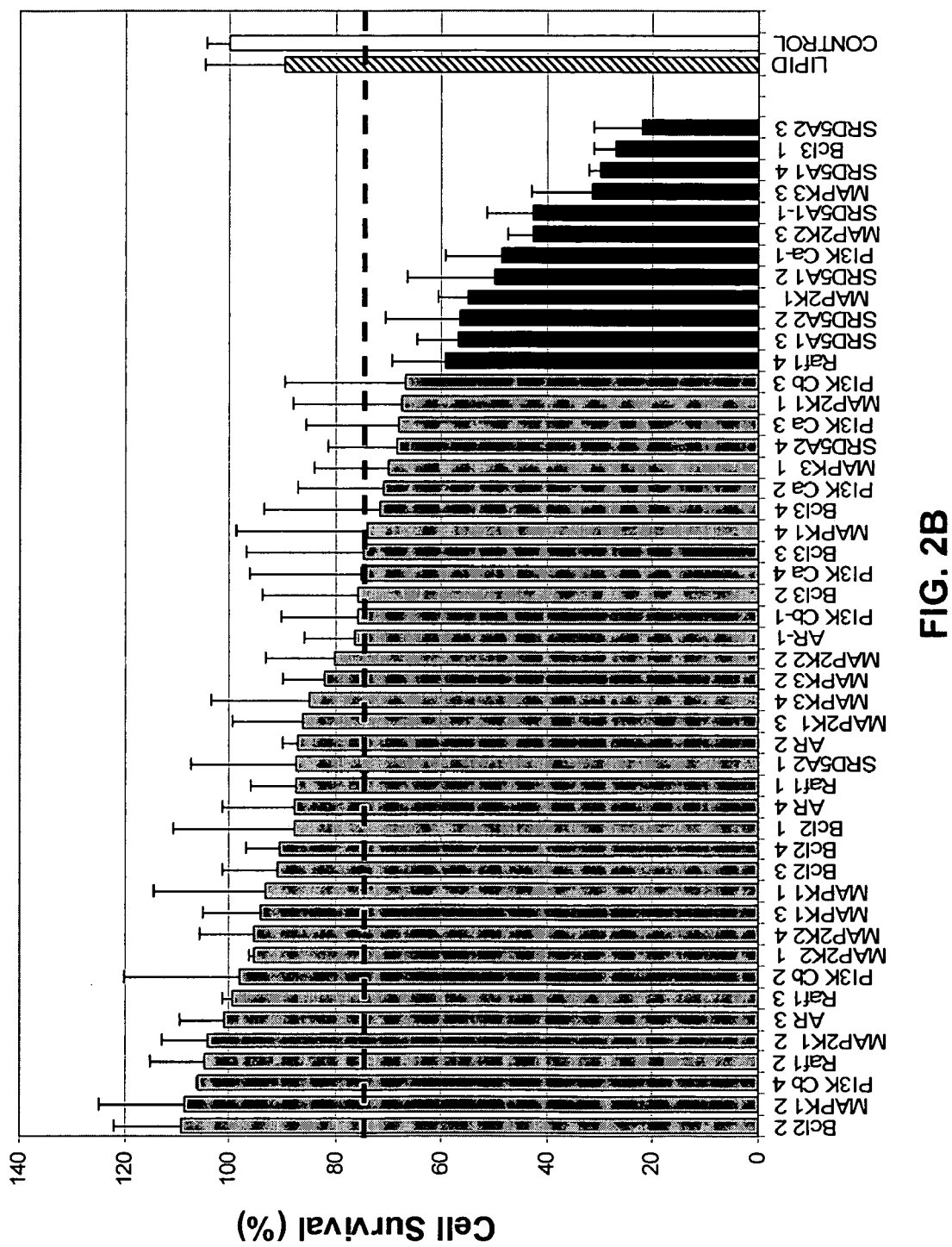

FIG. 2B is a graphical representation showing that cellular toxicity can be a consequence of off-targeting. The data was obtained from analysis of the individual siRNAs of 48 functional (e.g., >70% silencing) pools of four siRNA targeting 12 different genes. Only twelve of the forty-eight sequences (e.g., 25%) decreased cellular viability below 75%.

Figure 2C:
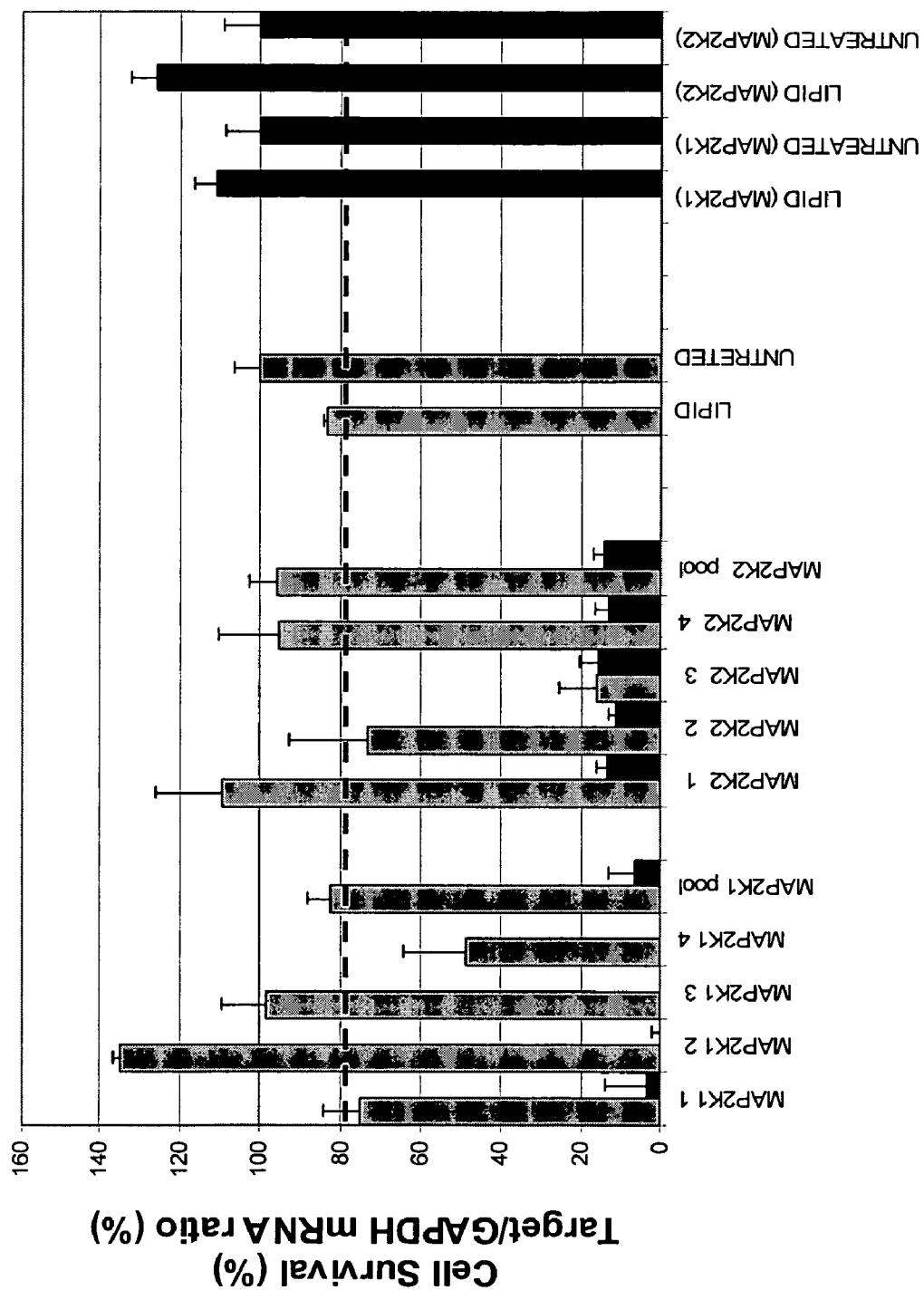

FIG. 2C is a graphical representation showing the off-targeting induced toxicity can be minimized or reduced by using pools of siRNA. As such, some exemplary siRNA depicted in FIG. 2B were pooled to reduce toxicity. While all eight duplexes targeting MAP2K1 and MAP2K2 show greater than 80% gene silencing, only a single siRNA in each quartet reduces cell viability below 75% (e.g., MAP2K1-d4 and MAP2K2-d3). Thus, as the remaining siRNAs in each group were equally functional, but non-toxic, the toxicity induced by MAP2K1-d4 and MAP2K2-d3 is unrelated to target knockdown.

Example 2

Figure 3:
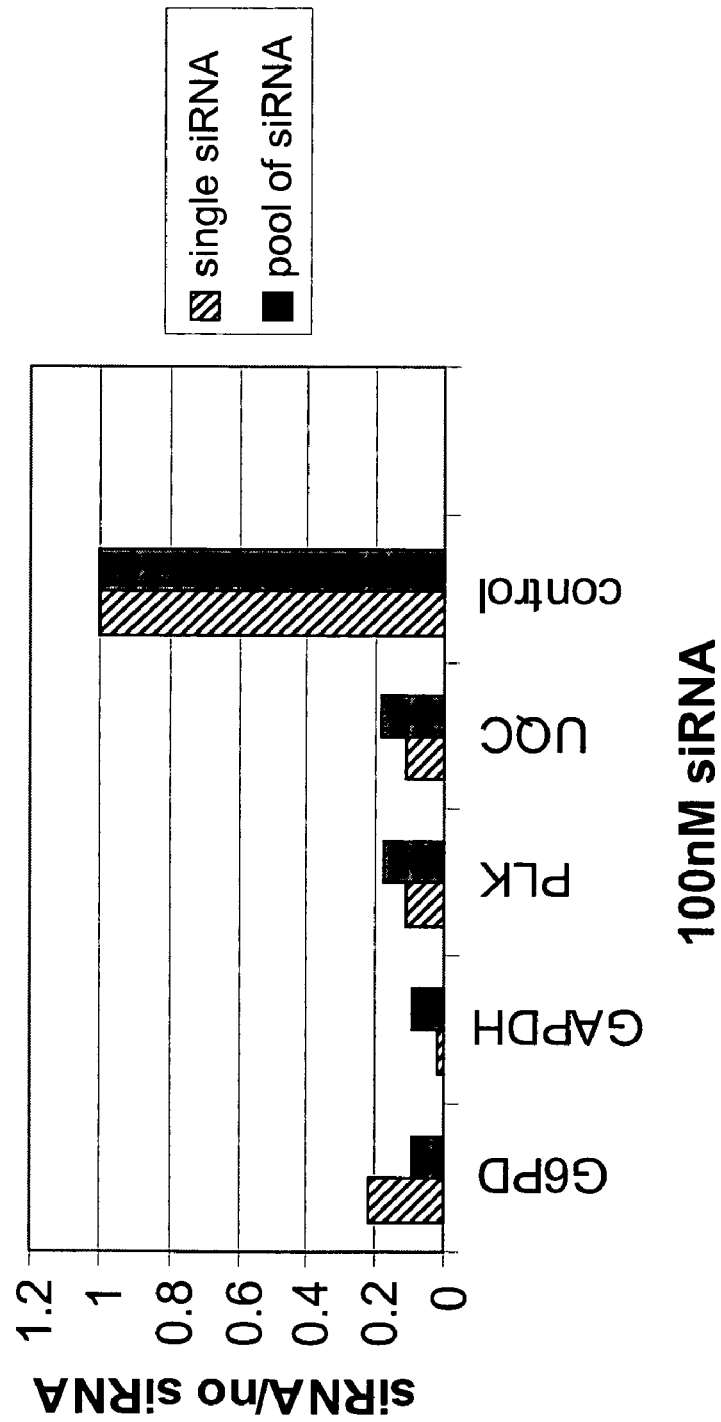
FIG. 3 is a graphical representation of an embodiment of the gene silencing of single and pooled siRNA.

The ability of rationally designed pools of siRNA to silence four separate genes simultaneously was studied with individual and pools of siRNAs targeting G6PD, GAPDH, PLK, and UQC. Pools of siRNA (e.g., 4 siRNA per gene) were forward transfected into cells at a total siRNA concentration of 100 nM, 6.25 nM per siRNA, using LIPOFECTAMINE™ 2000, and assayed twenty-four hours later by B-DNA. FIG. 3 is a graphical representation of the results which demonstrated that pools of rationally designed molecules are capable of simultaneously silencing four different genes. The ability to target multiple genes in an RTF format will significantly simplify the ability to use RTF for screening large (e.g., genome-sized) collections of siRNA.

Example 3

The genes involved in the kinase pathway are studied by siRNA RTF to determine the genes responsible for cell viability. Rationally designed pools of siRNAs targeting the 779 members of the kinase family are solubilized in RNase-free water and dried in individual wells of PLL coated 96-well plates. The amount of each pool of siRNA is a total of approximately 25 nM for 125 uL of total solution. A lipid solution having 0.1 ug of DharmaFECT™ 1 lipid in 25 uL total volume of Hanks Balanced Saline Buffer is added to each well and incubated for 20-40 minutes to solubilize and complex the siRNA before 10,000 HeLa cells in media are added for a final volume of 125 uL. The plates are maintained between 24 and 72 hours and assayed for cell viability. A comparison between the cell viability of cultures that were treated with lipid alone (i.e., control wells) and cultures treated with individual members of the Kinase siRNA array allows the identification of genes that are essential for HeLa cell viability.

Example 4

The genes involved in the cytokine receptor family are studied by siRNA RTF to determine the genes responsible for cell viability. Rationally designed pools of siRNAs targeting the 166 members of the cytokine receptor family are solubilized in RNase-free water and dried in individual wells of PLL coated 96-well plates. The amount of each pool of siRNA is a total of approximately 25 nM for 125 μL of total solution. A lipid solution having 0.1 ug of DharmaFECT™ 1 lipid in 25 uL total volume of Hanks Balanced Saline Buffer is added to each well and incubated for 20-40 minutes to solubilize and complex the siRNA before 10,000 HT-29 cells in media are added for a final volume of 125 uL. The plates are maintained between 24 and 72 hours and assayed for cell viability. A comparison between the cell viability of cultures that were treated with lipid alone (i.e., control wells) and cultures treated with individual members of the cytokine receptor siRNA array allows the identification of genes that are essential for HT-29 cell viability.

Example 5

The ability of a pool of siRNA to be directed against a selected gene was studied in an RTF protocol. To assess the effectiveness of pools of siRNA directed against a single target individual siRNAs and pools of three or four siRNAs directed against GAPDH, MAP2K1, or MAP2K2 were reverse transfected into 10,000 HeLa cells using DharmaFECT™ 1. At 48 hours after addition of cells the cultures were assessed for cell viability and target silencing knockdown (e.g., B-DNA assay). In this study, the siRNA are designated as follows: GAPDH siRNA duplex 1, duplex 2, duplex 3, and duplex 4; MAP2K1 siRNA duplex 1, duplex 2, duplex 4, and duplex 5; MAP2K2 siRNA duplex 1, duplex 2, duplex 4, and duplex 7.

Figure 4A:
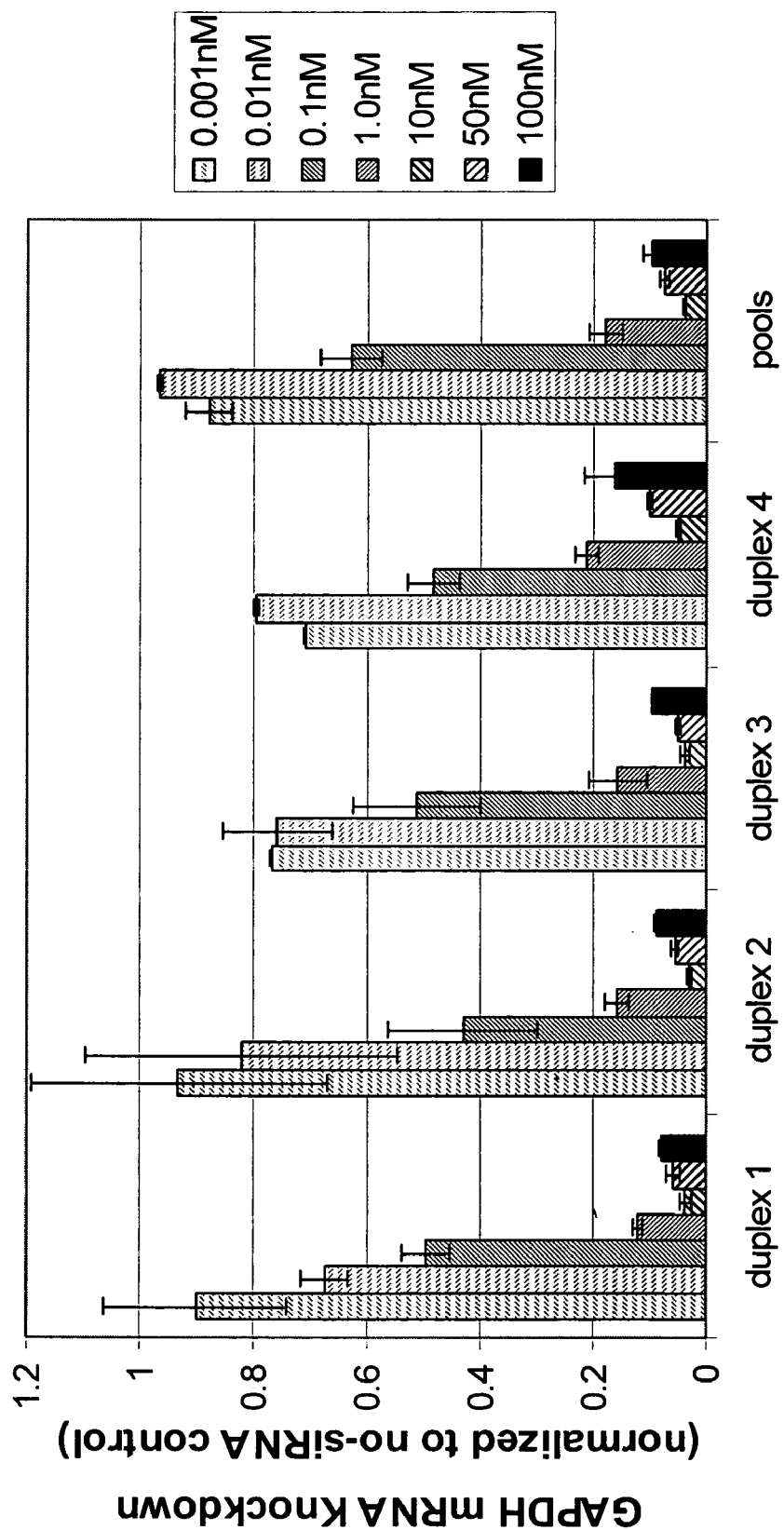
FIGS. 4A-4C are graphical representations of an embodiment of siRNA RTF protocols that compare the effectiveness of individual siRNA and pools of siRNA directed against, GAPDH, MAP2K2, and MAP2K1 at varying concentrations.
Figure 4B:
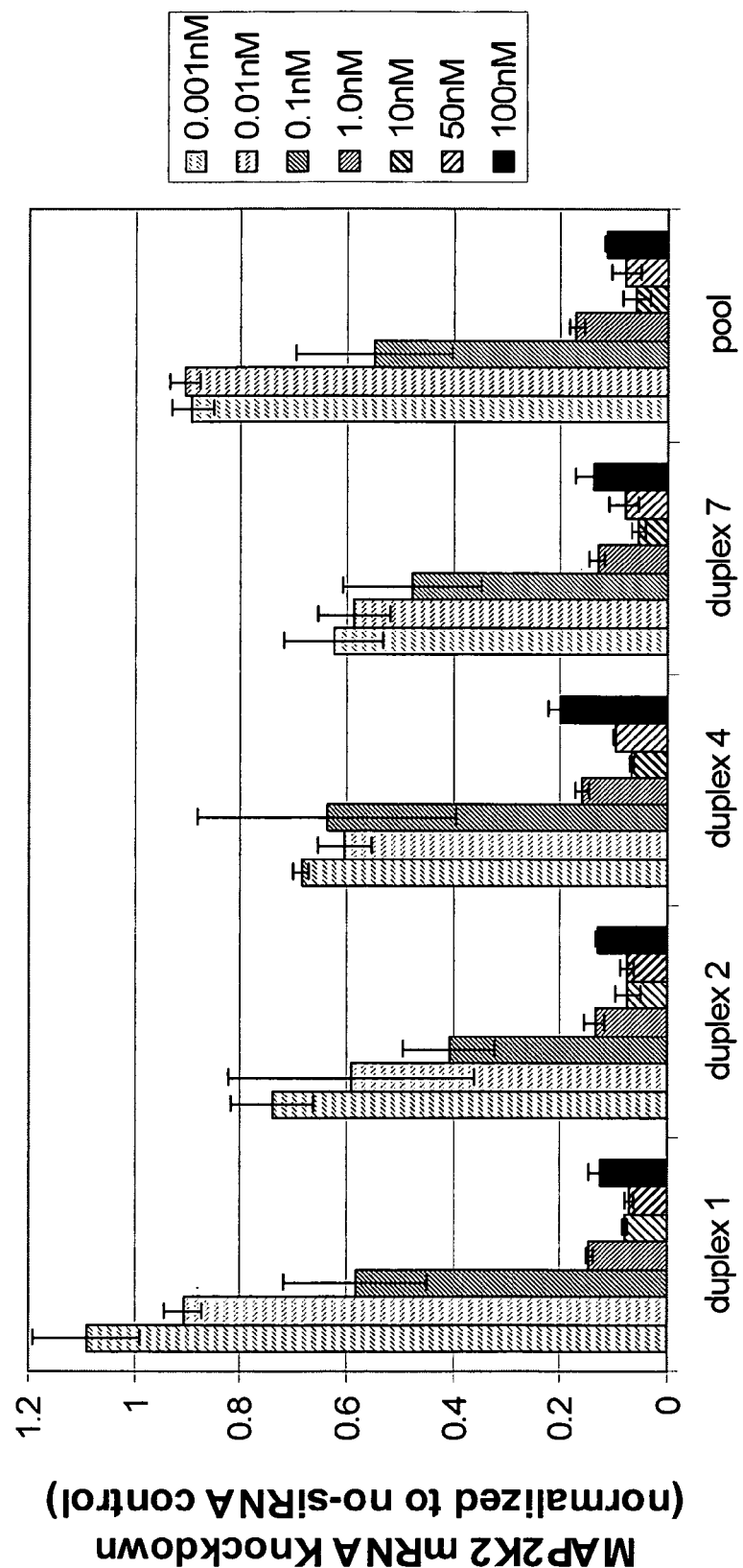
Figure 4C:
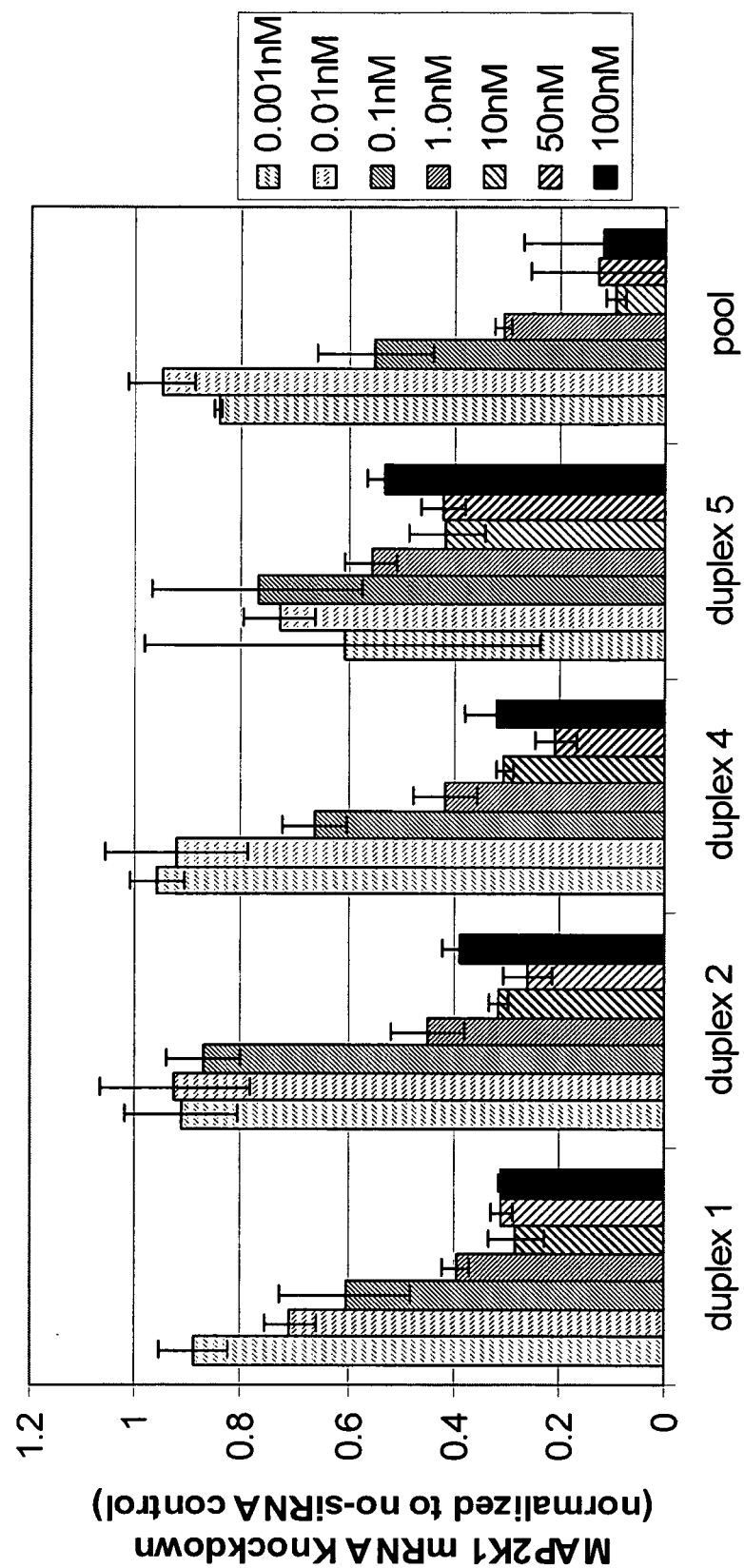

FIG. 4A is a graphical representation of results of an embodiment of GAPGH silencing that show pools act as well as or better than individual siRNA. FIG. 4B is a graphical representation of results of an embodiment of MAP2K2 silencing that show pools act as well as or better than individual siRNA. FIG. 4C is a graphical representation of results of an embodiment of GAPDH silencing that show pools act as well as or better than individual siRNA, where the pool provided superior silencing to any individual siRNA at 10 nM. In all of the cases tested, gene silencing using individual siRNA or pools did not alter overall cell toxicity (data not shown). Another benefit of pools involves the consistency of performance. For instance, while individual duplexes targeting GAPDH and MAP2K2 performed adequately (e.g., greater than 80% silencing at concentrations between 1 nM and 100 nM for all 8 siRNA), only a single siRNA (e.g., duplex 4) at a single concentration (e.g., 50 nM) provided greater then 80% silencing for MAP2K1. In contrast, pooled siRNA targeting all three targets generated 80% or greater silencing at concentrations of 10 nM, 50 nM and 100 nM. These results demonstrate that pooling can provides increased consistency in gene silencing in the RTF format.

Example 6

The ability of a pool of siRNA to be directed against a selected gene was studied in an RTF protocol. To assess the effectiveness of pools of siRNA directed against a single target combinations of individual siRNAs directed to multiple targets. The siRNA directed to GAPDH, MAP2K1, or MAP2K2 were reverse transfected into 10,000 HeLa cells using DharmaFECT™ 1 using a RTF procedure substantially similar to that described in Example 5.

Figure 5A:
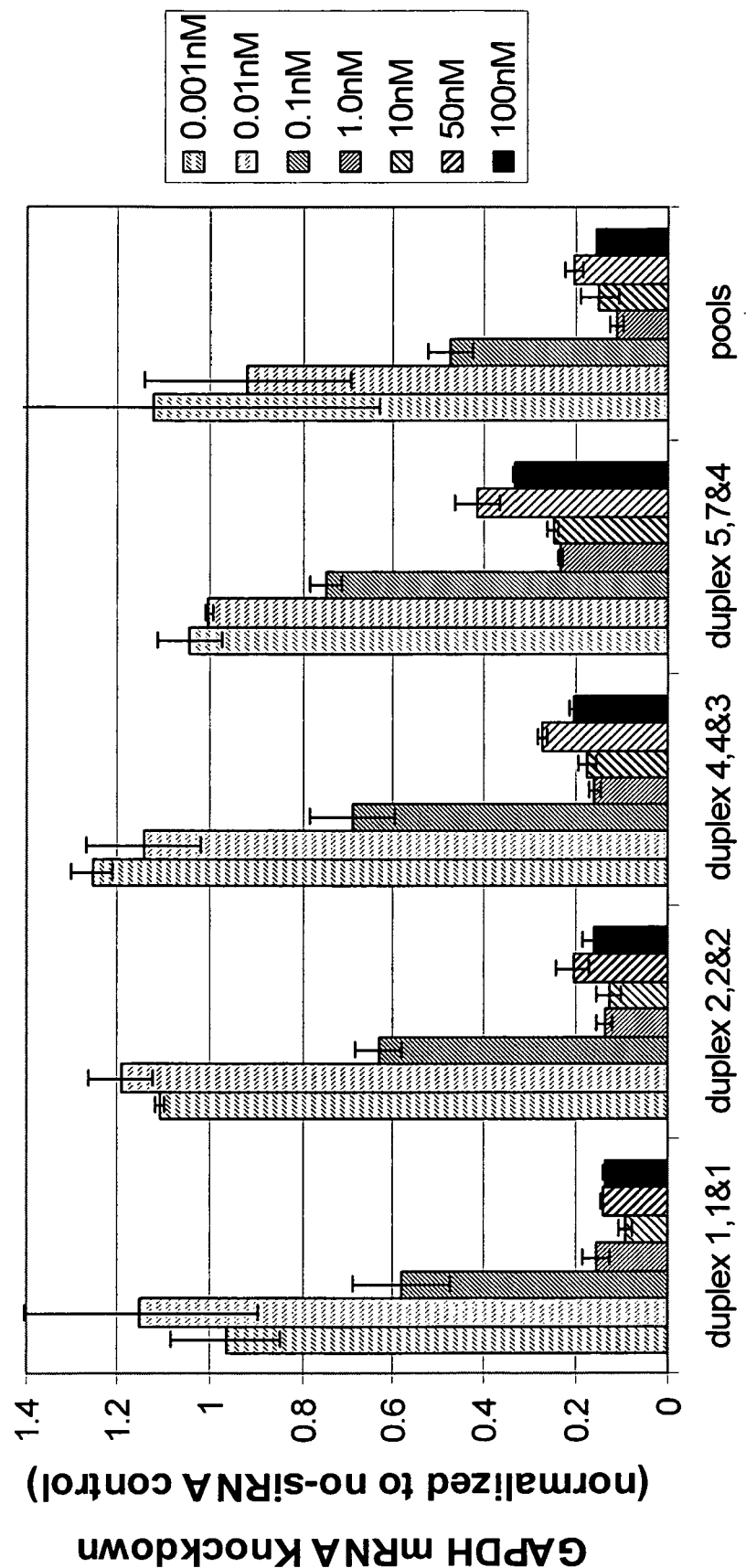
FIGS. 5A-5C are graphical representations of an embodiment of siRNA RTF protocols that compare the effectiveness of individual siRNA and pools of siRNA directed against, GAPDH, MAP2K2, and MAP2K1 at varying concentrations.
Figure 5B:
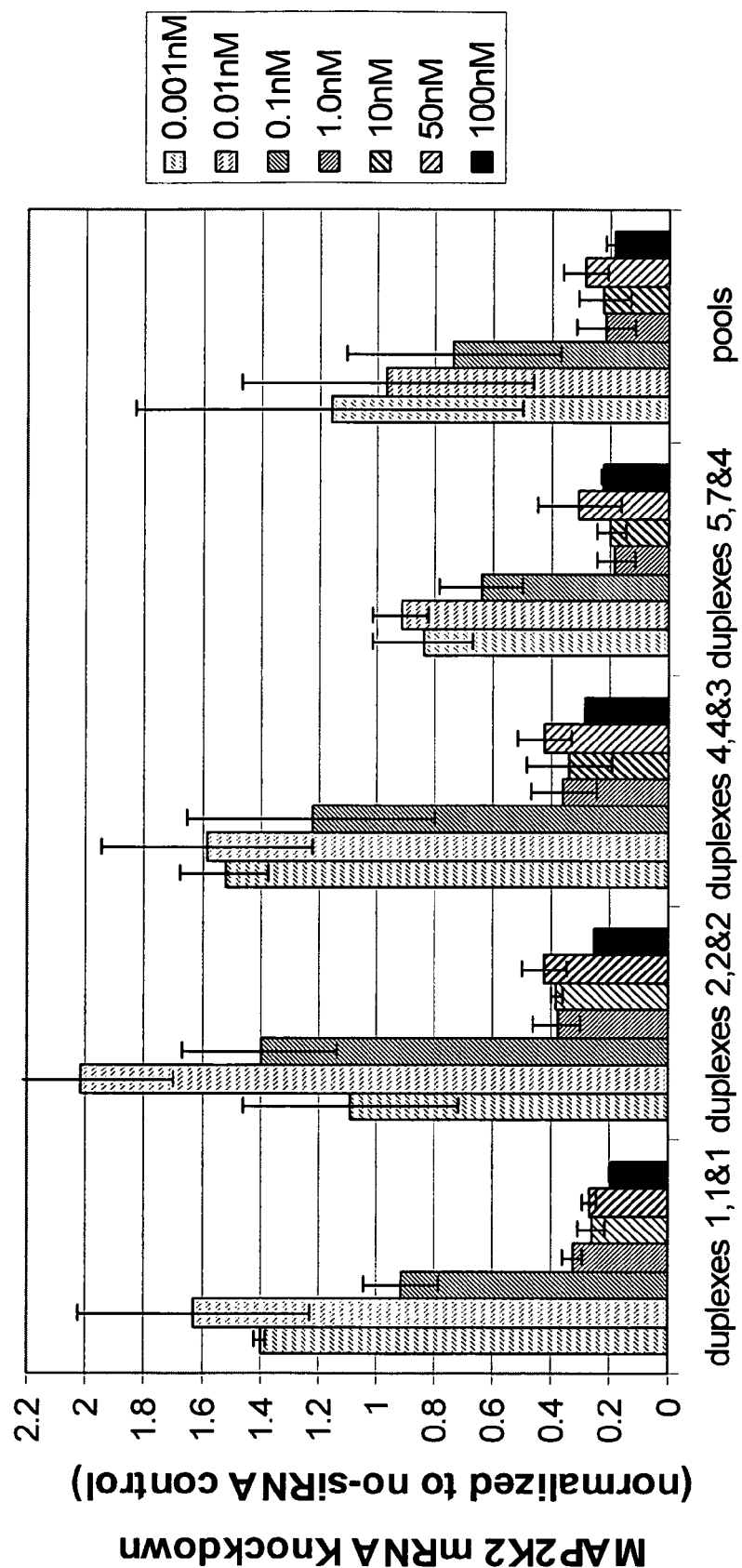
Figure 5C:
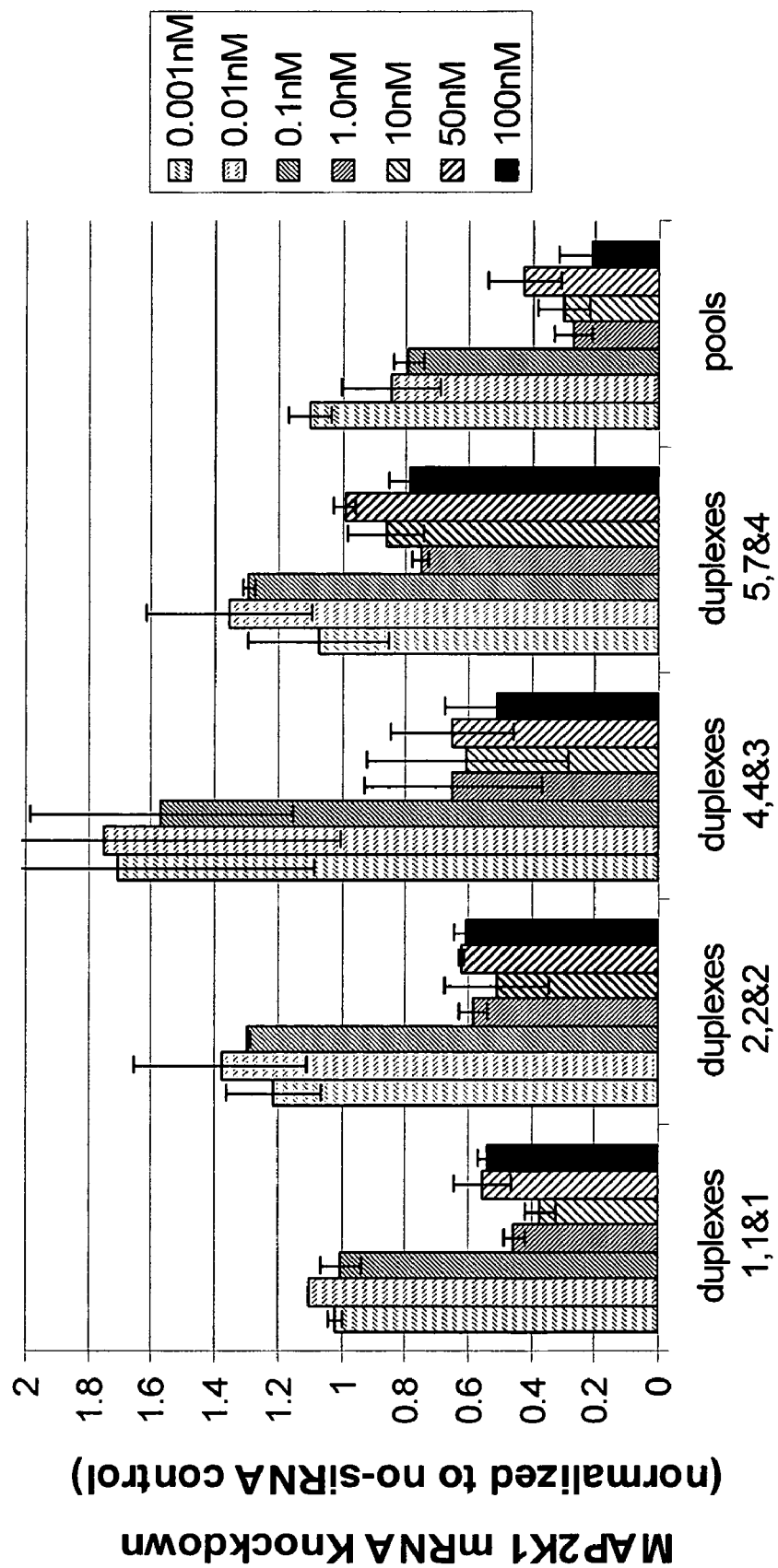

FIGS. 5A-5C are graphical representations that demonstrate that compatibility with multi-gene knockdown. FIG. 5A shows the GAPDH knockdown in the presence of GAPDH duplex 1, MAP2K2 duplex 1, and MAP2K1 duplex 1 (1, 1&1); and GAPDH knockdown in the presence of GAPDH duplex 2, MAP2K2 duplex 2, and MAP2K1 duplex 2 (2, 2&2); GAPDH knockdown in the presence of GAPDH duplex 4, MAP2K2 duplex 4, and MAP2K1 duplex 3 (4, 4&3); GAPDH knockdown in the presence of GAPDH duplex 5, MAP2K2 duplex 7, and MAP2K1 duplex 4 (5, 7&4); and GAPDH knockdown in the presence of GAPDH, MAP2K2, and MAP2K1 pools consisting of all of the before mentioned duplexes. FIG. 5B shows the MAP2K2 knockdown in the presence of all of the duplex combinations described in FIG. 5A. FIG. 5C shows the MAP2K1 knockdown in the presence of all the duplex combinations described in FIG. 5A. Greater than 75% silencing is achievable for all the GAPDH siRNA tested, even in the presence of competing siRNA directed against MAP2K1 and MAP2K2 targets. Similarly, greater than 75% silencing can be achieved for MAP2K2, even in the presence of siRNAs directed against GAPDH and MAP2K1. For MAP2K1, none of the individual siRNA provided greater than 75% silencing, but pools of MAP2K1 targeting siRNA were able to function adequately (at 1-100 nM) in the presence of pools of siRNA targeting GAPDH and MAP2K2. The compatibility of the invention with multi-gene targeting formats is a significant improvement, and allows users to simplify large genome-wide screens.

Example 7

A study was performed to determine whether pooling can reduce off-target effects. Briefly, four distinct siRNA that target human cyclophilin B were transfected into HeLa cells individually and as a pool (e.g., 96-well format, 20,000 cells per well, 100 nM for individual siRNA, 4×25 nM for pool of siRNAs) using Lipofectamine 2000 (0.5 uL per well). Twenty-four hours after transfection, cell lysates were collected (e.g., from 12 identically treated wells, Qiagen RLT buffer with BME) and total RNA was purified (Qiagen Rneasy columns with on-column Dnase digestion). RNA integrity was confirmed (RNA 6000 Nano LabChip, Agilent 2100 Bioanalyzer). For each sample, 650 ng of total RNA was amplified and Cy3- or Cy5-labeled using Agilent's Low Input RNA Fluorescent Linear Amplification Kit. Hybridizations were performed on Agilent's Human 1A (V2) Oligo Microarrays and the hybridization reference (Cy3) was mock-transfected cells. Slides were washed and dried using 6× and 0.06×SSPE with 0.025% N-lauroylsarcosine and Agilent's non-aqueous drying and stabilization solution, then scanned on an Agilent Microarray Scanner (model G2505B). The raw image was processed using Feature Extraction (v7.5.1.). Further analysis was conducted using Spotfire Decision Site 8.1 and the Spotfire Functional Genomics Module. Spots flagged as outliers on any of the arrays used in comparative analysis (for instance a heatmap of 10 arrays) were not considered. A 2-fold cutoff (Log Ratio of >0.3 or <−0.3) was applied to genes used in comparative analysis.

Results of these studies show that a pool of siRNA can limit the number of off-targeted genes in comparison to an individual siRNA having the same target gene. While two different individual siRNAs had limited off-target profiles, some individual siRNAs silenced large numbers of genes. In contrast, the number of off-targeted genes resulting from transfection of the different pools of siRNAs had low numbers of genes that were silenced, and hence less off-targeting. Thus pooling can reduce the number of off-targets in a gene silencing study.

Example 8

In one example, a multi-well RTF plate or series of plates can be designed in order to optimize RTF with siRNA. Accordingly, the plates can be configured to include any of the following variables: (1) the concentration of pools of siRNA can be between 0.01-250 nM, more preferably between 0.05 and 100 nM, even more preferably between 0.1 and 50 nM, still even more preferably between 0.5 and 25 nM, and most preferably between 0.75 and 10 nM or about 1 nM; (3) the types of polynucleotide carrier can be a lipid such as DharmaFECT™ 1, DharmaFECT™ 2, DharmaFECT™ 3, or DharmaFECT™ 4; (3) the concentration of the lipid polynucleotide carrier can be at concentrations of 0.05-1 ug per 100 uL of solution, more preferably at concentrations of 0.05-0.5 ug of lipid per 100 uL of solution, even more preferably still at concentrations of 0.05-0.25 ug of lipid per 100 uL of solution, and most preferably at concentrations of 0.05-0.1 ug per 100 uL of solution; (4) the types of media and/or buffer used to complex the lipid can be preferably Opti-MEM™, more preferably HyQ-MEM™, and most preferably buffered salt solutions such as Hanks Buffered salt solution or equivalent mixtures; and (5) the types and amounts of cells having densities of 1,000 to 35,000 cells per about 0.3 $cm^2$ to about 0.35 $cm^2$ preferred densities of 2,000-30,000 cells, more preferably 2,000-20,000 cells, even more preferably 2,000-15,000 cells, and most preferably cell densities of 2,000-10,000 cells per about 0.3 $cm^2$ to about 0.35 $cm^2$. The siRNA can be used to study the silencing of selected target genes, or control siRNA can be used to silence known genes in a reproducible manner.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of reverse transfection for introducing siRNA into a cell to effect gene silencing, the method comprising:
providing a well plate, the well plate having a plurality of wells with a dried gene silencing composition deposited in at least one well having at least one siRNA which is capable of silencing a target gene, the at least one siRNA comprising:
a sense strand having 2'-O-methyl modifications on the first and second 5' nucleotides; and
an antisense strand having a 2'-O-methyl modification on the second 5' nucleotide and a 5' end phosphate;
wherein the sense region and the antisense region are capable of forming a duplex of 18-26 base pairs of nucleotides, and wherein nucleotides of the sense strand and antisense strand other than the first 5' sense nucleotide, the second 5' sense nucleotide, and the second 5' antisense nucleotide include a 2'-OH;
adding an aqueous medium to the at least one well so as to suspend or solubilize the at least one siRNA into the aqueous medium; and
adding cells to the at least one well having the suspended or solubilized at least one siRNA under conditions that permit the at least one siRNA to be introduced into the cell and to effect gene silencing.

2. A method as in claim 1, further comprising:
selecting a suitable polynucleotide carrier, wherein selecting is a function of at least one of transfection technique, siRNA composition, or cell type being transfected;
and adding a cationic polynucleotide carrier to the at least one well so as to form a siRNA-carrier complex, wherein the polynucleotide carrier is added either before, during, or after adding the aqueous medium to the at least one well, and wherein the siRNA-carrier complex is suspended or solubilized in the aqueous medium.

3. A method as in claim 2, wherein the polynucleotide carrier includes a lipid.

4. A method as in claim 1, further comprising silencing production of a target polypeptide by at least 50%.

5. A method as in claim 4, further comprising silencing production of the target polypeptide by at least 80%.

6. A method as in claim 1, wherein the cells are added in an amount of about $2\times10^3$ to about $3\times10^4$ cells per 0.35 $cm^2$ of cell growth surface area.

7. A method as in claim 1, wherein the well plate has been stored in a sealed package.

8. A method as in claim 7, wherein the sealed package contains an inert gas therein.

9. A method as in claim 7, wherein the sealed package is vacuum sealed.

10. A method as in claim 7, wherein the well plate has been stored in the sealed package at room temperature.

11. A method as in claim 10, wherein the well plate is shipped in the sealed package at ambient temperature.

12. A method as in claim 1, wherein the dried gene silencing composition is characterized as being spotted on a floor of a well of the well plate such that the dried gene silencing composition does not flow or displace from the well floor when the well plate is tilted or inverted.

13. A method of reverse transfection for introducing siRNA into a cell to effect gene silencing, the method comprising:
providing a well plate contained in a sealed, sterile package, said well plate having a plurality of wells containing a dried gene silencing composition, the dried gene silencing composition comprising:
at least one siRNA that is capable of silencing a target gene, said siRNA being capable of being solubilized or suspended in an aqueous medium in a known amount for transfecting cells when deposited in an individual well of the well plate, the at least one siRNA comprising:
a sense strand having 2'-O-methyl modifications on the first and second 5' nucleotides; and
an antisense strand having a 2'-O-methyl modification on the second 5' nucleotide and a 5' end phosphate;
wherein the sense region and the antisense region are capable of forming a duplex of 18-26 base pairs of nucleotides, and wherein nucleotides of the sense strand and antisense strand other than the first 5' sense nucleotide, the second 5' sense nucleotide, and the second 5' antisense nucleotide include a 2'-OH;
adding an aqueous medium to at least one of the wells having the dried gene silencing composition so as to suspend or solubilize the at least one siRNA into the aqueous medium; and
adding cells to the at least one well having the suspended or solubilized at least one siRNA under conditions that permit the at least one siRNA to be introduced into the cell and to effect gene silencing.

14. The method of claim 13 further comprising, adding a cationic polynucleotide carrier either before, during, or after adding the aqueous medium to the at least one well, wherein the polynucleotide carrier includes at least one compound selected from the group consisting of cationic polymers, lipids, lipopolymers, lipid-peptide mixtures, and cholesterol.

15. The method as in claim 13, wherein the providing includes obtaining a well plate that has been stored in the sealed, sterile package at a temperature of up to at least about 37° C. while maintaining functionality of the at least one siRNA in the at least one well.

16. A method of reverse transfection for introducing siRNA into a cell to effect gene silencing, the method comprising:
providing a well plate contained in a sealed package, said well plate having a plurality of wells, each well containing a substantially dried gene silencing composition having at least one siRNA which is capable of silencing a target gene, said siRNA being capable of being solubilized or suspended in an aqueous medium in a known amount for transfecting cells when deposited in an individual well of the well plate, the at least one siRNA comprising:
a sense strand having 2'-O-methyl modifications on the first and second 5' nucleotides; and
an antisense strand having a 2'-O-methyl modification on the second 5' nucleotide and a 5' end phosphate;
wherein the sense region and the antisense region are capable of forming a duplex of 18-26 base pairs of nucleotides, and wherein nucleotides of the sense strand and antisense strand other than the first 5' sense nucleotide, the second 5' sense nucleotide, and the second 5' antisense nucleotide include a 2'-OH;
unsealing the package to expose the wells;
adding an aqueous medium containing a cationic polynucleotide carrier compound to at least one of the wells so as to suspend or solubilize the at least one siRNA into the aqueous medium; and
adding cells to the at least one well having the suspended or solubilized at least one siRNA under conditions that permit the at least one siRNA to be introduced into the cell and to effect gene silencing.

17. The method of claim 16, wherein the cationic polynucleotide carrier compound includes at least one compound selected from the group consisting of cationic polymers, lipids, lipopolymers, lipid-peptide mixtures, and cholesterol.

18. The method as in claim 17, wherein the cationic polynucleotide carrier compound includes a lipid.

19. The method as in claim 16, wherein the providing includes obtaining a well plate that has been stored in the sealed, sterile package at a temperature of up to at least about 37° C. while maintaining functionality of the at least one siRNA in the at least one well.

* * * * *